United States Patent
Sirico et al.

(10) Patent No.: US 11,574,269 B2
(45) Date of Patent: Feb. 7, 2023

(54) CONTROLLER AND METHOD USING MACHINE LEARNING TO OPTIMIZE OPERATIONS OF A PROCESSING CHAIN OF A FOOD FACTORY

(71) Applicant: Worximity Technologies Inc., Montreal (CA)

(72) Inventors: Louis Sirico, Montreal (CA); Yannick Desmarais, Montreal (CA)

(73) Assignee: WORXIMITY TECHNOLOGIES INC., Montreal (CA)

(*) Notice: Subject to any disclaimer, the term of this patent is extended or adjusted under 35 U.S.C. 154(b) by 59 days.

(21) Appl. No.: 17/179,450

(22) Filed: Feb. 19, 2021

(65) Prior Publication Data

US 2021/0264334 A1 Aug. 26, 2021

Related U.S. Application Data

(60) Provisional application No. 62/979,523, filed on Feb. 21, 2020, provisional application No. 63/082,496, filed on Sep. 24, 2020.

(51) Int. Cl.
*G05B 13/02* (2006.01)
*G06Q 10/06* (2012.01)
(Continued)

(52) U.S. Cl.
CPC ..... *G06Q 10/0633* (2013.01); *G05B 13/0265* (2013.01); *G05B 19/418* (2013.01);
(Continued)

(58) Field of Classification Search
CPC ......... G06Q 10/0633; G06Q 10/06393; G06Q 50/04; G06Q 50/28; G05B 13/0265;
(Continued)

(56) References Cited

U.S. PATENT DOCUMENTS

2010/0138026 A1\* 6/2010 Kaushal ................... G06N 5/04
706/23
2014/0022093 A1\* 1/2014 Hubauer ............ G05B 19/4183
340/870.02
(Continued)

FOREIGN PATENT DOCUMENTS

GB 2512087 \* 12/2020
JP WO 2019/198772 \* 10/2019

*Primary Examiner* — Hien D Khuu
(74) *Attorney, Agent, or Firm* — IP Delta Plus Inc.

(57) ABSTRACT

Computing device and method using machine learning to optimize operations of a processing chain of a food factory. The computing device collects data representative of characteristics of a product processed by the processing chain. At least some of the collected data are received from one or more sensor monitoring operations of the processing chain. The computing device determines at least one product characteristic value based on the collected data. The computing device executes the machine learning inference engine, which uses a predictive model for inferring command(s) for controlling processing appliance(s) of the processing chain based on inputs. The inputs comprise the at least one product characteristic value. The computing device transmits the command(s) to the processing appliance(s) of the processing chain. Examples of product characteristic values comprise: a product temperature, a product humidity level, a product geometric characteristic, a product weight, and a product defect measurement.

21 Claims, 16 Drawing Sheets

(51) Int. Cl.
  *G06N 3/04* (2006.01)
  *G06Q 50/04* (2012.01)
  *G06Q 50/28* (2012.01)
  *G05B 19/418* (2006.01)
  *G01N 33/00* (2006.01)

(52) U.S. Cl.
  CPC ......... *G06N 3/04* (2013.01); *G06Q 10/06393* (2013.01); *G06Q 50/04* (2013.01); *G06Q 50/28* (2013.01); *G01N 33/004* (2013.01)

(58) Field of Classification Search
  CPC ........ G05B 19/418; G05B 2219/33041; G05B 19/41865; G05B 19/41885; G06N 3/04; G06N 3/084; G06N 3/0454; G01N 33/004
  USPC .......................................................... 700/96
  See application file for complete search history.

(56) References Cited

U.S. PATENT DOCUMENTS

| | | | |
|---|---|---|---|
| 2019/0118443 A1* | 4/2019 | Asaoka | B29C 45/76 |
| 2019/0150028 A1* | 5/2019 | Gervais | H04W 48/18 |
| | | | 370/235 |
| 2021/0049460 A1* | 2/2021 | Ahn | G06N 3/006 |
| 2021/0063041 A1* | 3/2021 | Lupien | G05B 15/02 |

* cited by examiner

CONTROLLER AND METHOD USING MACHINE LEARNING TO OPTIMIZE OPERATIONS OF A PROCESSING CHAIN OF A FOOD FACTORY

TECHNICAL FIELD

The present disclosure relates to the field of automated food factories. More specifically, the present disclosure relates to a controller and method using machine learning to optimize operations of a processing chain of a food factory.

BACKGROUND

A processing chain of a food factory comprises a plurality of processing appliances. Each processing appliance implements a given step in the process of transforming one or more raw or pre-processed product into a refined product. For example, a processing chain is used for transforming potatoes into fries by means of a plurality of operations (e.g. inspecting, sorting, cleaning, peeling, slicing, mixing, cooking, drying, packaging, etc.), each operation being performed by a dedicated processing appliance.

The optimization of the operations of the processing chain is generally based on a control equipment executing an algorithm for controlling one or more processing appliances of the processing chain. The algorithm implements a set of rules for processing data received from one or more sensor, to generate commands for controlling one or more processing appliance.

However, a set of rules is not always an adequate tool for taking into consideration the complexity of the interactions between parameters influencing the operations of the processing chain. In particular, it is at least difficult and sometimes impossible for a human being, to design a set of rules capable of modelling the influence of a combination of parameters on the operations of the processing chain. Current advances in artificial intelligence, and more specifically in machine learning technologies (e.g. neural networks), can be taken advantage of for solving this type of optimization problem.

Therefore, there is a need for a new controller and method using machine learning to optimize operations of a processing chain of a food factory.

SUMMARY

According to a first aspect, the present disclosure relates to a computing device comprising at least one communication interface, memory for storing a predictive model, and a processing unit comprising one or more processor. The processing unit is configured to collect data representative of characteristics of a product processed by a processing chain. At least some of the collected data are received via the at least one communication interface from one or more sensor monitoring operations of the processing chain. The processing unit is configured to determine at least one product characteristic value based on the collected data. The processing unit is configured to execute a machine learning inference engine, the machine learning inference engine using the predictive model for inferring one or more output based on inputs. The inputs comprise the at least one product characteristic value. The one or more output comprises one or more command for controlling at least one processing appliance of the processing chain. The processing unit is configured to transmit via the at least one communication interface the one or more command to the at least one processing appliance of the processing chain.

According to a second aspect, the present disclosure relates to a method using machine learning to optimize operations of a processing chain. The method comprises storing a predictive model in a memory of a computing device. The method comprises collecting by a processing unit of the computing device data representative of characteristics of a product processed by the processing chain. At least some of the collected data are received via at least one communication interface of the computing device from one or more sensor monitoring operations of the processing chain. The method comprises determining by the processing unit of the computing device at least one product characteristic value based on the collected data. The method comprises executing by the processing unit of the computing device a machine learning inference engine, the machine learning inference engine using the predictive model for inferring one or more output based on inputs. The inputs comprise the at least one product characteristic value. The one or more output comprises one or more command for controlling at least one processing appliance of the processing chain. The method comprises transmitting by the processing unit of the computing device via the at least one communication interface of the computing device the one or more command to the at least one processing appliance of the processing chain.

According to a third aspect, the present disclosure relates to a non-transitory computer program product comprising instructions executable by a processing unit of a computing device, the execution of the instructions by the processing unit providing for using machine learning to optimize operations of a processing chain by implementing the aforementioned method.

In a particular aspect, the machine learning inference engine is a neural network inference engine implementing a neural network using the predictive model for inferring the one or more output based on the inputs, the predictive model comprising weights of the neural network.

In another particular aspect, the processing chain is located in a food factory and the product is a food product.

In still another particular aspect, the at least one product characteristic value comprises at least one of the following: a temperature of the product, a humidity level of the product, a geometric characteristic of the product, a weight of the product, a tensile strength of the product, an internal pressure of the product, and a defect measurement for the product.

In yet another particular aspect, the one or more command controls a functionality implemented by the at least one processing appliance, the functionality comprising inspecting, sorting, cleaning, cutting, peeling, slicing, blending, mixing, blanching, cooking, baking, frying, heating, cooling, freezing, humidifying, or packaging.

BRIEF DESCRIPTION OF THE DRAWINGS

Embodiments of the disclosure will be described by way of example only with reference to the accompanying drawings, in which.

DETAILED DESCRIPTION

Figure 1:
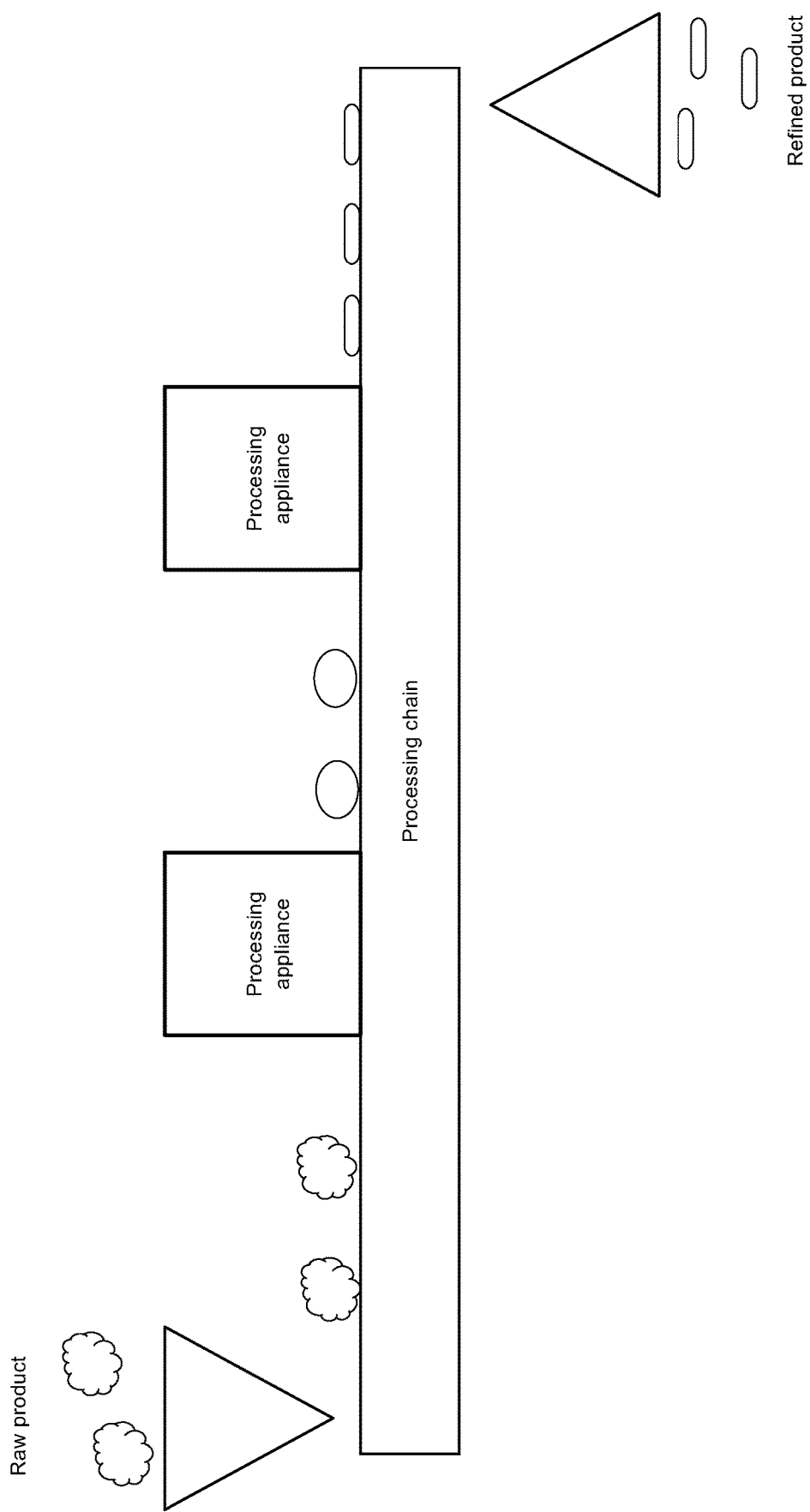
FIG. 1 illustrates a processing chain of a food factory comprising a plurality of processing appliances.

The foregoing and other features will become more apparent upon reading of the following non-restrictive description of illustrative embodiments thereof, given by way of example only with reference to the accompanying drawings.

Various aspects of the present disclosure generally address one or more of the problems related to an optimization of the operations of a processing chain of a food factory. The optimization is based on the usage of a machine learning technology (e.g. a neural network) using data captured by sensors (and optionally additional data) for generating command(s) to control operations of processing appliance(s) of the processing chain. The machine learning technology may also be used to predict a yield, a quality metric, or a carbon dioxide ($CO_2$) footprint associated to the processing chain of the food factory.

Throughout the present specification and claims, the following definitions are used:

Functionality: operation performed by a processing appliance, such as for example: inspecting, sorting, sieving, measuring, weighing, disinfecting, cleaning, peeling, slicing, shredding, crushing, grinding, mixing, blending, kneading, emulsifying, marinating, pickling, blanching, cooking, baking, frying, drying, cooling, freezing, packaging, canning, vacuum sealing, etc.

Operating condition: measurable, quantifiable and/or verifiable state or factor defining current operation of a processing appliance and/or a processing chain.

Operating parameter: an adjustable or configurable feature of a processing appliance and/or of a processing chain.

Pre-processed product: any food product that is inputted into the processing chain, which is not raw product, as well as any food product outputted by one of the processing appliances and still requiring to be further processed by another processing appliance to produce the refined product.

Processing appliance: device or apparatus designed to perform at least one functionality.

Processing chain: refers to a set of processing appliances, and a food processing factory may include multiple processing chains operating independently, concurrently, sequentially or interdependently.

Product characteristic: a measurable or quantifiable or verifiable feature or quality of a raw product, a pre-processed product and/or a refined product.

Product characteristic value: any of a measurable, quantifiable, verifiable or subjective comparator provided by a sensor, a scanner, measuring device quantifier or comparing device.

Raw product: refers to raw produce and pre-processed food product to be processed by the process chain Refined product: food product produced by the processing chain.

Stock Keeping Unit (SKU): a scannable code which may be applied to a raw product, a pre-processed product or to a refined product directly or to a container of the raw product, the pre-processed product or the refined product. The SKU typically includes a barcode and/or an alphanumeric combination of characters. The SKU allows automatic tracking of the origin and product characteristics of the raw product, the pre-processed product and the refined product. The SKU may further be used as a product characteristic by the present controller and method, and/or to define the product characteristics of the refined product to be produced.

To avoid any confusion throughout the present specification, the expression refined product is used only to refer to the final product produced by the processing chain, while the expression pre-processed product is used to refer to any food that is not a raw product and enters into the processing chain for being processed, and any food product outputted by one processing appliance which is not yet the refined product and still requires to be inputted in at least one other processing appliance.

Referring now to FIG. 1, a schematic representation of a processing chain of a food factory is represented. A raw or pre-processed product enters the processing chain and a refined product exits the processing chain. In the rest of the description, a food factory transforming potatoes into fries will be used as an example only, where raw potatoes enter the processing chain and fries exit the processing chain, but the present controller and method are not limited to transforming potatoes and may be used for processing any type of raw product or food product and/or to produce any refined product.

The processing chain includes a plurality of processing appliances. Each processing appliance performs a step of the process implemented by the processing chain for transforming the raw and/or pre-processed product(s) into the refined product. Each processing appliance receives an input and processes the input to generate an output. For example, the first appliance represented in FIG. 1 receives the raw or pre-processed product, transforms the raw or pre-processed product into a partially refined product, and outputs the partially refined product. The second appliance represented in FIG. 1 receives the partially refined product, transforms the partially refined product into the refined product, and outputs the refined product.

Although the present specification describes and illustrates the present controller, method and processing chain as inputting one raw or pre-processed product, recourse to the singular form and to one product (raw or pre-processed product) as an input to the processing chain or as the input to any of the processing appliance is herein made in the singular form for simplicity purposes only, as the present controller, method and resulting processing chain may rely on multiple inputs of raw product(s) and/or pre-processed product(s) either inputted initially or consecutively at any step of the processing chain to produce the refined product.

FIG. 1 represents a basic processing chain including only two processing appliances for illustration purposes only. A person skilled in the art would readily understand that a processing chain may include any number of processing appliances to perform the transformation of the raw or pre-processed product(s) into the refined product. Some of the appliances of the processing chain may also operate in parallel, to perform a particular step of the transformation process in parallel.

In the exemplary context of a food factory transforming potatoes into fries, the following processing appliances may be included in the processing chain. The following description of sequentially operating processing appliances is for illustration purposes only, and does not aim at being perfectly representative of a processing chain transforming potatoes into fries. A first processing appliance performs an inspection of the potatoes as they enter the food processing chain, to identify characteristics such as geometry, temperature, weight, brix, humidity, or any other defects. A second processing appliance sorts the potatoes to eliminate potatoes which have too many defects (e.g. potatoes which are molded, rotted, infected with insets, or have even been partially consumed by rodents). A third processing appliance washes/cleans the sorted potatoes. A fourth processing appliance steam cooks/peels the cleaned potatoes. A fifth processing appliance cuts/slices the partially cooked/peeled potatoes. At this stage, the cut/sliced potatoes can be referred to as fries, since they now have the shape of fries. A sixth processing appliance cooks the fries. A seventh processing appliance dries the cooked fries (to eliminate cooking oil). The dried cooked fries constitute the refined product exiting the processing chain. An eighth processing appliance packages the fries. The processing appliances of the present processing chain operate based on the refined product to be produced, and more particularly, to the SKU of the refined product being produced. The SKU may provide information on the origin and/or particular quality or requirement of the raw product and/or pre-processed product being used (for example: country of origin, freshness level, organic, vegan, etc.)

One objective of the owner of the food factory is to optimize the operations of the processing chain, and more specifically to optimize the operations of at least some of the processing appliances involved in the processing chain. The optimization process is based on one or more metric representative of the efficiency of the processing chain. The optimization consists in fine-tuning the operations of at least some of the processing appliances to improve the one or more metric.

One metric which can be used for evaluating the efficiency of the processing chain is the yield of the processing chain. For example, the yield of the processing chain is calculated by dividing a weight of refined product exiting the processing chain by a weight of raw or pre-processed product(s) used for producing the refined product. For example, 100 kilograms of raw product (for example potatoes) enter the processing chain over a given time period (e.g. one minute) and 60 kilograms of refined product (e.g. fries) exit the processing chain after processing of the initial 100 kilograms of raw product by the processing chain. In this case, the yield is 0.6 or 60%.

The owner of the food factory defines a nominal yield, for example 65%. The nominal yield can be achieved with the raw or pre-processed product meeting a set of pre-defined quality criteria. If a batch of raw or pre-processed product does not meet the set of pre-defined quality criteria, the achieved yield is lower (e.g. only 55%). In order to compensate the lack of quality of the raw or pre-processed product, the operation of one or more of the processing appliances is adapted, to compensate for the lack of quality of the raw or pre-processed product. Adapting the operation of a processing appliance consists in adapting operating parameters of the processing appliance (e.g. adapting the duration of an operation performed by the processing appliance, adapting a temperature at which the processing appliance operates, adjusting the amount of water or product filler added to the product to compensate for dryness, etc.). By performing this adaption process on the processing chain, the yield can be improved (e.g. reach a yield of 60% with the adaptation process instead of 55% without the adaptation process).

For scalability reasons, it may be more effective to define a nominal yield for a given processing appliance of the processing chain, and to adapt the operation of the given processing appliance to be as close as possible to the nominal yield of the given processing appliance. For example, for a processing chain comprising a large number of processing appliances, it may be difficult to evaluate the impact of each processing appliance on the global yield of the processing chain. Thus, one or more local yield measurement corresponding to respective one or more processing appliance is defined, and acted upon. In this case, the yield of a given processing appliance is calculated by dividing a weight of product exiting the processing appliance by a weight of product entering the given processing appliance for producing the weight of product exiting the given processing appliance. Referring to the previous example, a nominal yield could be defined for the fourth processing appliance, consisting of a weight of sliced potatoes produced by the fourth processing appliance divided by a weight of peeled potatoes used by the fourth processing appliance for producing the weight of sliced potatoes.

Another objective of the owner of the food factory is to provide an accurate level of safety for the refined product exiting the processing chain, based on safety standards defined by regulation authorities for the food industry. For this purpose, samples of the refined product are collected and evaluated, to determine their level of safety. The level of safety can be defined as a percentage. Bellow a given percentage (e.g. 95%), the refined product is not safe and should be discarded.

The process of evaluating the safety of the refined product is often performed manually and has an important cost for the owner of the food factory. However, the safety evaluation must be performed thoroughly, since the impact of selling a refined product not safe for consumption is devastating.

The operating conditions of the processing appliances and of the processing chain have a direct impact on the safety level of the refined product. For example, if one of the processing appliances is not operating in nominal conditions, the safety level of the refined product may not meet the required standard. Thus, by monitoring the operating conditions of one or more processing appliance of the processing chain, it is possible to predict that the safety level may not meet the required standard. In this case, more time and resources shall be spent on the evaluation of the refined product exiting the processing chain.

In order to better control operations of the processing appliances and of the processing chain, sensors are deployed at various stages of the processing chain. The sensors monitor various operating conditions of one or more processing appliance and/or of the processing chain. Based on data provided by the sensors, operating parameters of a given processing appliance or of the processing chain as a whole may be modified. A software is generally used for this purpose. The software implements an algorithm (e.g. an expert system) which uses as inputs the data collected by the sensors and generates outputs parameters and/or commands for modifying the operating parameter(s) of the given processing appliance.

However, such a software is very difficult to implement and usually does not provide a sufficient adaptation/adjustments due to the vast number of possible conditions/situations. The implementation of the software is usually based on a compromise, between a very complex software capable of dealing with multiple situations with a good level of granularity, and a simpler software which is less costly to implement (and more reliable) but does not provide an accurate level of granularity. The complexity of the software is due to the fact that many operating conditions (collected by the sensors) are taken into consideration, and it is difficult for a human being to evaluate the impact of these operating conditions when they are considered in combination.

In this context, the usage of artificial intelligence means, and more specifically of the neural network technology, is more adapted than a traditional control software using inputs to generate outputs. The neural network technology relies on the collection of a large amount of data during a training phase, which are used for training a neural network. The result of the training phase is a predictive model generated by the neural network. Then, during an operational phase, the neural network uses the predictive model to generate outputs (e.g. commands for controlling a given processing appliance and operating parameters thereof) based on inputs (e.g. data collected by sensors monitoring operating conditions of the processing chain 10).

Although the rest of the disclosure is based on the usage of a neural network, a person skilled in the art would readily understand that other machine learning technologies may be used in place of a neural network, such as a decision tree, a support vector machine, a regression analysis, a Bayesian network, a causality analysis, etc.

Optimization of Processing Appliance Operations

Figure 2:
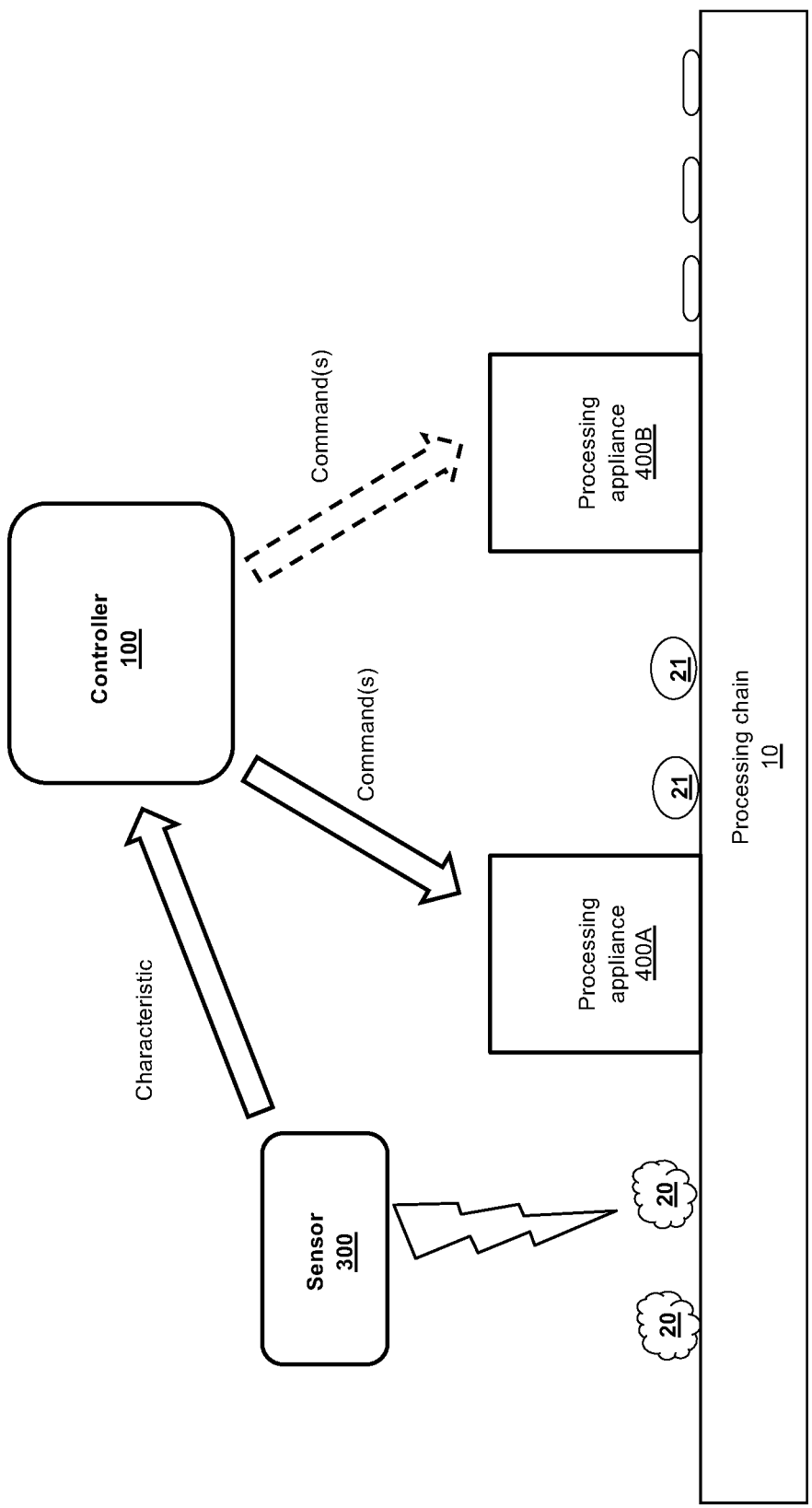
FIGS. 2 and 3 illustrate the processing chain of FIG. 1 where a controller and several sensors are deployed.

Reference is now made concurrently to FIGS. 1 and 2. The processing chain 10 represented in FIG. 2 corresponds to the processing chain represented in FIG. 1. The processing appliances 400A and 400B represented in FIG. 2 correspond to the processing appliances represented in FIG. 1. The raw product 20 and the pre-processed product 21 (hereinafter the products 20 and 21) carried by the processing chain 10 represented in FIG. 2 correspond to the products carried by the processing chain represented in FIG. 1.

The products 20 are carried by the processing chain 10 to the processing appliance 400A, where they are processed. The processing of the products 20 by the processing appliance 400A generates the products 21. The products 21 are carried by the processing chain 10 to the processing appliance 400B, where they are processed. For example, the products 20 and 21 represent potatoes are different stages of the transformation process from a raw potato to a fry.

A sensor 300 collects data related to the products 20 and transmits the collected data to a controller 100. The collected data represent a characteristic of the products 20 (e.g. temperature, humidity level, geometric characteristic, weight, tensile strength, internal pressure, defect measurement, etc.). Details of the sensor 300 will be provided later in the description. Although a single sensor 300 is represented in FIG. 2 for simplification purposes, a plurality of sensors 300 may be collecting various types of data related to the products 20 and transmitting the collected data to the controller 100.

The controller 100 processes the data related to the products 20, collected by the sensor(s) 300 to generate command(s) for controlling the processing appliance 400A such as for example the operating parameter(s) thereof. Optionally, the data (related to the products 20) collected by the sensor(s) 300 are also used to generate command(s) for controlling other processing appliance(s) (e.g. 400B). Details of the controller 100 will be provided later in the description.

Figure 3:
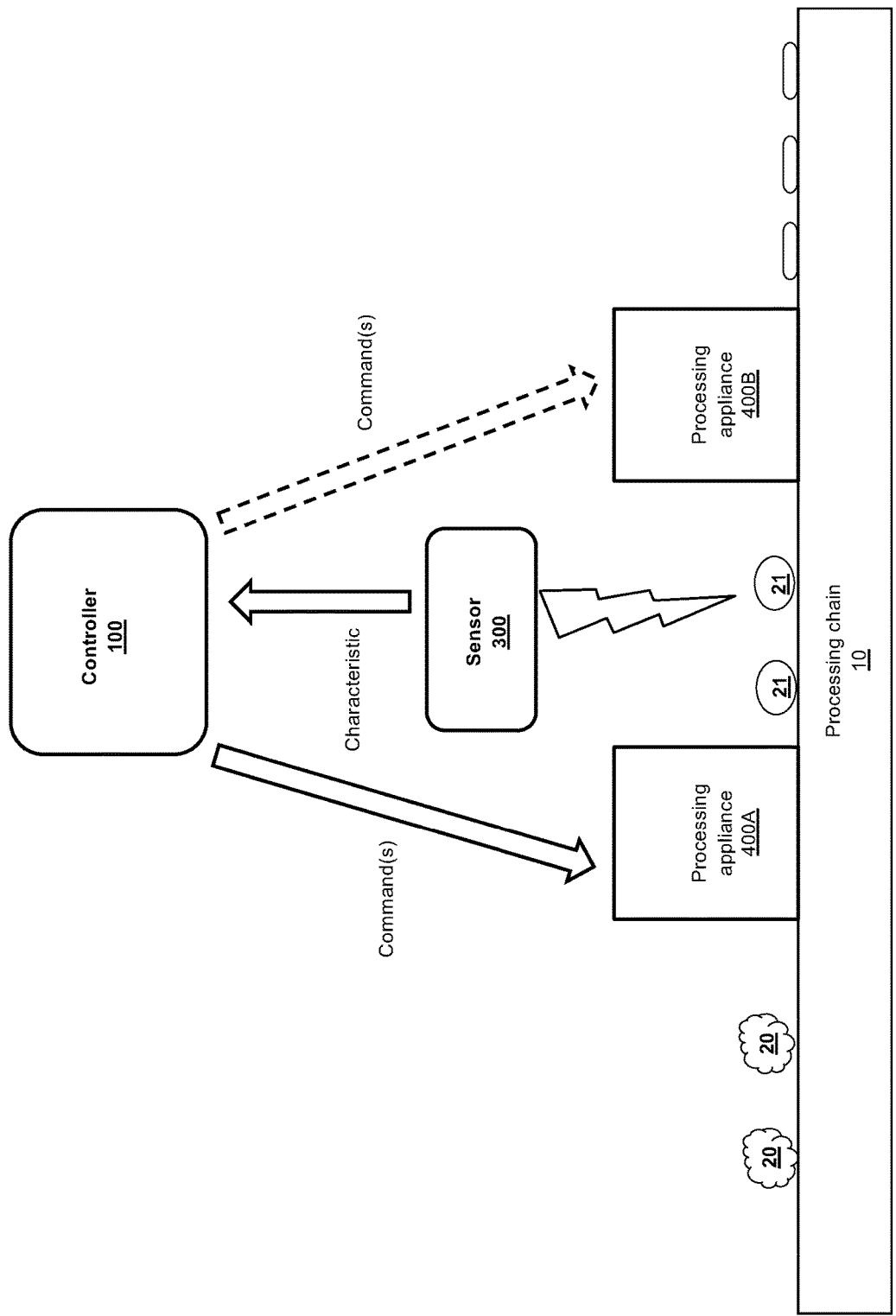

Reference is now made concurrently to FIGS. 1, 2 and 3. FIG. 3 represents a configuration where the sensor 300 collects data related to the products 21. The command(s) generated by the controller 100 for controlling the processing appliance 400A (and optionally the processing appliance 400B) are based on data related to the products 21, collected by the sensor 300.

FIGS. 2 and 3 illustrate different configurations, where the data collected by the sensors 300 for controlling a given processing appliance may be related to products at different stages of the processing chain 10.

For example, as illustrated in FIGS. 2 and 3, the controller 100 generates command(s) for controlling the processing appliance 400A based on data related only to products 20 (entering the processing appliance 400A), data related only to products 21 (exiting the processing appliance 400A), or data related to a combination of products 20 and 21.

In another example illustrated in FIGS. 2 and 3, the controller 100 generates command(s) for controlling the processing appliance 400B based on data related only to products 21 (entering the processing appliance 400B), or data related to a combination of products 20 (entering the processing appliance 400A) and 21 (entering the processing appliance 400B).

Figure 4:
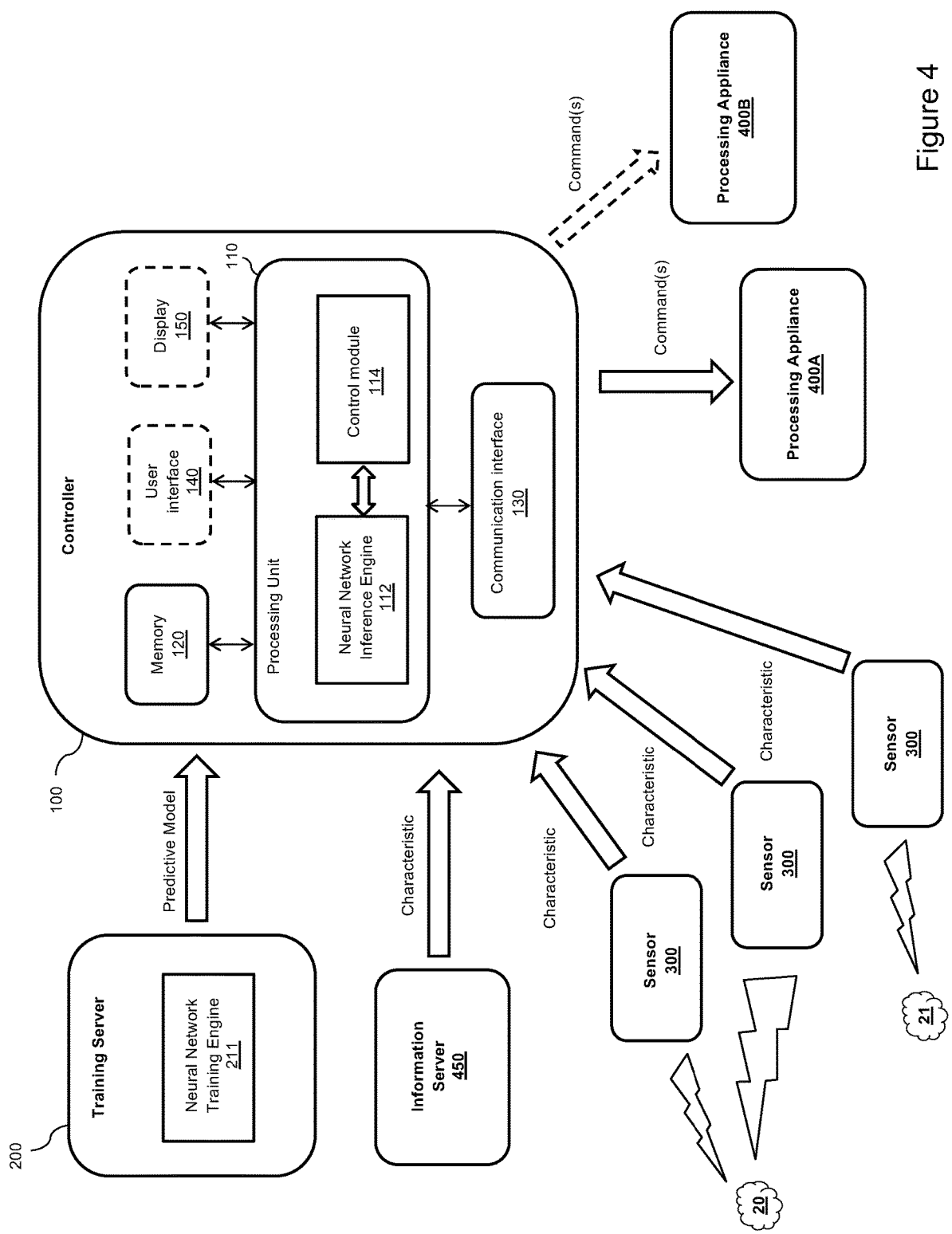
FIG. 4 illustrates components of the controller represented in FIGS. 2 and 3.
Figure 5:
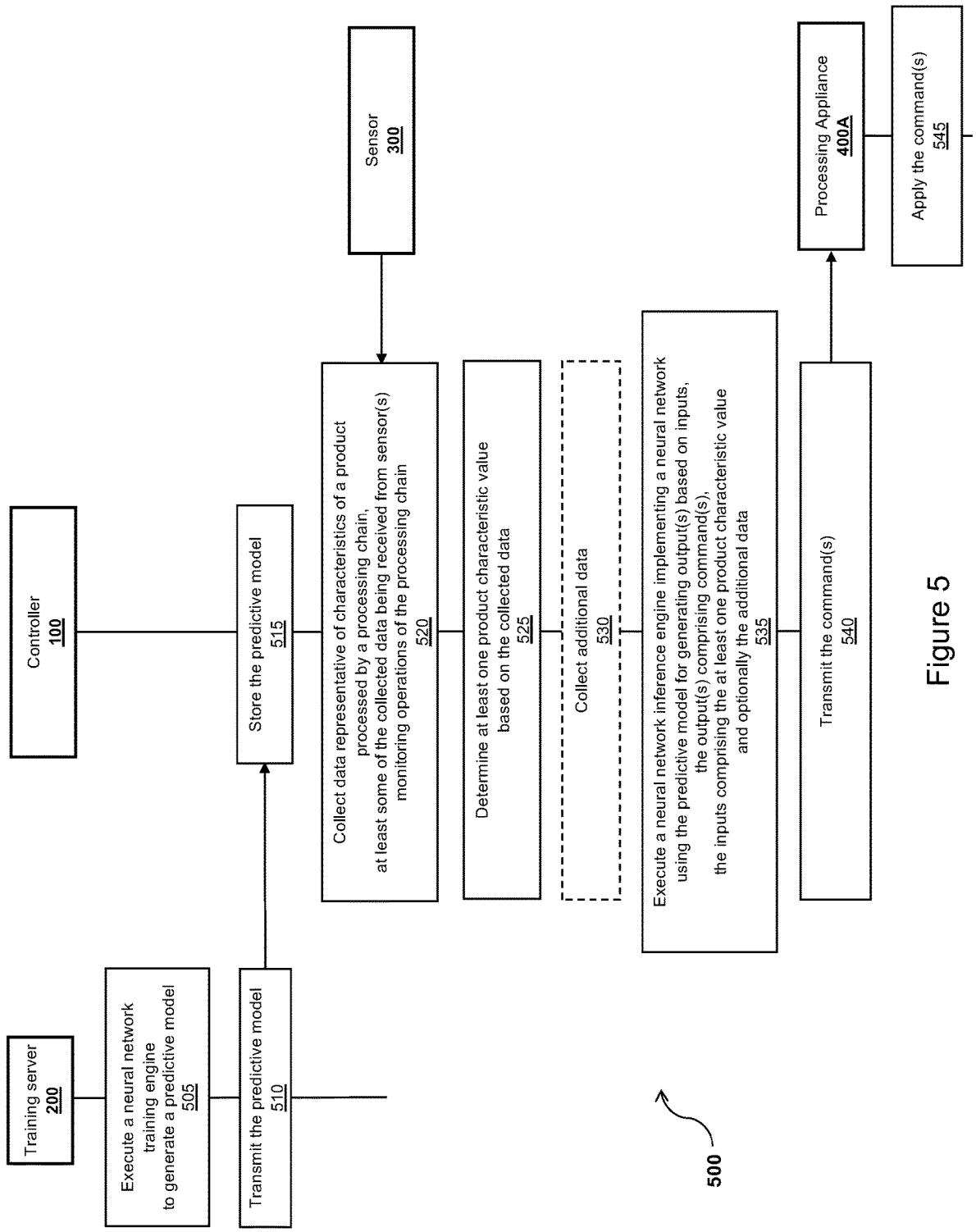
FIG. 5 illustrates a method using a neural network to optimize operations of the processing chain of FIGS. 2 and 3.

Reference is now made concurrently to FIGS. 1, 2, 3, 4 and 5. FIG. 4 represents details of the environment controller 100 of FIGS. 2 and 3, and FIG. 5 represents a method 500 using a neural network for optimizing operations of the processing chain 10.

The controller 100 comprises a processing unit 110, memory 120, a communication interface 130, optionally a user interface 140, and optionally a display 150. The controller 100 may comprise additional components not represented in FIG. 4 for simplification purposes (e.g. an additional communication interface 130). The controller 100 may consist of one of the following computing devices: a computer, a server, a mobile computing device, etc.

The processing unit 110 comprises one or more processors (not represented in FIG. 4) capable of executing instructions of a computer program. Each processor may further comprise one or several cores.

The memory 120 stores instructions of computer program(s) executed by the processing unit 110, data generated by the execution of the computer program(s), data received via the communication interface 130, etc. Only a single memory 120 is represented in FIG. 4, but the controller 100 may comprise several types of memories, including volatile memory (such as a volatile Random Access Memory (RAM), etc.) and non-volatile memory (such as a hard drive, solid-state drive (SSD), electrically-erasable programmable read-only memory (EEPROM), flash, etc.).

The communication interface 130 allows the controller 100 to exchange data with several devices (e.g. a training server 200, one or more sensor 300, one or more processing appliance 400A and 400B, etc.) over one or more communication network (not represented in FIG. 4 for simplification purposes). The term communication interface 130 shall be interpreted broadly, as supporting a single communication standard/technology, or a plurality of communication standards/technologies. Examples of communication interfaces 130 include a wireless (e.g. Wi-Fi, cellular, wireless mesh, etc.) communication module, a wired (e.g. Ethernet) communication module, a combination of wireless and wired communication modules, etc. In an exemplary configuration, the communication interface 130 of the controller 100 has a first wireless (e.g. Wi-Fi) communication module for exchanging data with the sensor(s) and the processing appliance(s), and a second wired (e.g. Ethernet) communication module for exchanging data with the training server 200. The communication interface 130 usually comprises a combination of hardware and software executed by the hardware, for implementing the communication functionalities of the communication interface 130.

At least some of the steps of the method 500 are implemented by the controller 100, making use of a neural network to optimize operations of the processing chain 10.

A dedicated computer program has instructions for implementing at least some of the steps of the method 500. The instructions are comprised in a non-transitory computer program product (e.g. the memory 120) of the controller 100. The instructions, when executed by the processing unit 110 of the controller 100, provide for making use of a neural network to optimize operations of the processing chain 10. The instructions are deliverable to the controller 100 via an electronically-readable media such as a storage media (e.g. CD-ROM, or any internally or externally attached storage device connected via USB, Firewire, SATA, etc.), or via communication links (e.g. via a communication network through the communication interface 130).

The dedicated computer program product executed by the processing unit 110 comprises a neural network inference engine 112 and a control module 114.

Also represented in FIG. 4 is the training server 200. Although not represented in FIG. 4 for simplification purposes, the training server 200 comprises a processing unit, memory and a communication interface. The processing unit of the training server 200 executes a neural network training engine 211.

The execution of the neural network training engine 211 generates a predictive model, which is transmitted to the controller 100 via the communication interface of the training server 200. For example, the predictive model is transmitted over a communication network and received via the communication interface 130 of the controller 100.

Also represented in FIG. 4 are the sensors 300 introduced in FIGS. 2 and 3. Although not represented in FIG. 4 for simplification purposes, the sensors 300 comprise at least one sensing module for detecting a characteristic of the products (e.g. 20 or 21) carried by the processing chain 10, and a communication interface for transmitting to the controller 100 data representative of the detected characteristic of the products. The data representative of the characteristic of the products are transmitted over a communication network and received via the communication interface 130 of the controller 100. The sensors 300 may also comprise a processing unit for generating the data representative of the characteristic of the products based on raw data provided by the sensing module.

In the rest of the description, data representative of a characteristic of the products and transmitted by a sensor 300 to the controller 100 will be referred to as a product characteristic value.

A first example of sensor 300 consists of a temperature sensor, capable of measuring a temperature of the products (e.g. 20 or 21) and transmitting the measured temperature to the controller 100. The temperature sensor measures a series of temperatures as the products circulate on the processing chain 10. The series of measured temperatures is transmitted to the controller 100. Alternatively, the temperature sensor calculates an average temperature for the products over a given period of time (e.g. every minute) based on the series of temperatures measured over the given period of time. The average temperature is transmitted to the controller 100. The processing unit 110 of the controller 100 may also calculate the average temperature based on the series of measured temperatures transmitted by the temperature sensor. A temperature sensor capable of measuring a temperature of a remote object is well known in the art. For example, the temperature sensor is an infrared temperature sensor using an infrared beam for measuring the surface temperature of the products.

A second example of sensor 300 consists of a humidity sensor, capable of measuring a humidity level of the products (e.g. 20 or 21) and transmitting the measured humidity level to the controller 100. The humidity sensor measures a series of humidity levels as the products circulate on the processing chain 10. The series of measured humidity levels is transmitted to the controller 100. Alternatively, the humidity sensor calculates an average humidity level for the products over a given period of time (e.g. every minute) based on the series of humidity levels measured over the given period of time. The average humidity level is transmitted to the controller 100. The processing unit 110 of the controller 100 may also calculate the average humidity level based on the series of measured humidity levels transmitted by the humidity sensor. A humidity sensor capable of measuring a humidity level of a remote object is well known in the art. For example, the humidity sensor uses optical measurements (e.g. optical fiber based sensor) to evaluate the humidity level of the remoted object.

A third example of sensor 300 consists of a geometry sensor, capable of determining a geometric characteristic value of the products (e.g. 20 or 21) and transmitting the geometric characteristic value to the controller 100. The geometry sensor determines a series of geometric characteristic values as the products circulate on the processing chain 10. The series of determined geometric characteristic values is transmitted to the controller 100. Alternatively, the geometry sensor determines an average geometric characteristic value for the products over a given period of time (e.g. every minute) based on the series of geometric characteristic values determined over the given period of time. The average geometric characteristic value is transmitted to the controller 100. The processing unit 110 of the controller 100 may also calculate the average geometric characteristic value based on the series of determined geometric characteristic values transmitted by the geometry sensor. Examples of geometric characteristic of the products include a volume of the products, a size of the products (e.g. length and/or width and/or height of the products), an area of the products, a shape of the products, etc.

The implementation of the geometry sensor may be more or less complex, based on its capabilities. For example, the geometry sensor may use a combination of camera(s), light(s), and pattern recognition software (e.g. implementing a neural network model), etc., for determining the geometric characteristics of the objects. Consequently, in the context of the present disclosure, a sensor 300 shall be interpreted as potentially including several devices cooperating for determining an object characteristic value. For example, one or more cameras collaborate with a pattern recognition software executed by a processing unit. In an exemplary implementation, an integrated geometry sensor is used. The integrated geometry sensor includes a detection device (e.g. a line-scan camera, a laser scanner for 2D/3D profile measurements, etc.) capturing raw data and a processing unit executing dedicated software(s) for generating the geometric characteristic values based on the captured raw data. In an alternative implementation, the processing unit executing the dedicated software(s) is not integrated with the detection device capturing the raw data (e.g. the dedicated software is executed by the processing unit 110 of the controller, or by the processing unit of an intermediate computing device (not represented in FIG. 4) interfaced with the detection device and the controller 100).

A fourth example of sensor 300 consists of a weighting sensor, capable of measuring a weight of the products (e.g. 20 or 21) and transmitting the measured weight to the controller 100. The weighting sensor measures a series of weights as the products circulate on the processing chain 10. The series of measured weights is transmitted to the controller 100. Alternatively, the weighting sensor calculates an average weight (or a cumulative weight) for the products over a given period of time (e.g. every minute) based on the series of weights measured over the given period of time. The average (or cumulative) weight is transmitted to the controller 100. The processing unit 110 of the controller 100 may also calculate the average (or cumulative) weight based on the series of measured weights transmitted by the weighting sensor. A weighting sensor capable of determining a weight of objects carried by a processing chain is also well known in the art.

A fifth example of sensor 300 consists of a defect sensor, capable of determining a defect measurement for the products (e.g. 20 or 21) and transmitting the defect measurement to the controller 100. The defect sensor determines a series of defect measurements as the products circulate on the processing chain 10. The series of determined defect measurements is transmitted to the controller 100. Alternatively, the defect sensor determines an average defect measurement for the products over a given period of time (e.g. every minute) based on the series of defect measurements determined over the given period of time. The average defect measurement is transmitted to the controller 100. The processing unit 110 of the controller 100 may also calculate the average defect measurement based on the series of determined defect measurements transmitted by the defect sensor. Examples of defects include a shape of the product considered as inappropriate, a color of the product considered as inappropriate, the presence of a stain on the surface of the product, etc. For a given type of defect, a measurement adapted to the given type of defect is determined, such as an average number of occurrences of the given type of defect per product, or a percentage of products presenting the given type of defect. The implementation of the defect sensor is similar to the implementation of the geometry sensor.

The aforementioned examples of sensors 300 are for illustration purposes only. A person skilled in the art would readily understand that other types of sensors 300 could be used in the context of the processing chain 10 managed by the controller 100. For example, at least one of a temperature/a humidity level/a lighting level, in the area where the processing chain 10 is operating, can be measured by a dedicated sensor (not represented in FIG. 4 for simplification purposes) and transmitted to the controller 100. The temperature and/or humidity level in the area is different from the previously mentioned temperature or humidity level (measured by one of the sensors 300) of the products carried by the processing chain 10.

Furthermore, each product characteristic value may consist of either a single value (e.g. the average temperature of the products is 19 degrees Celsius), or a range of values (e.g. the average temperature of the products is within the range of 18 to 20 degrees Celsius).

Also represented in FIG. 4 are the processing appliances 400A and 400B introduced in FIGS. 2 and 3. Although not represented in FIG. 4 for simplification purposes, the processing appliances 400A and 400B comprise at least one actuation module, and a communication interface for receiving one or more command from the controller 100. The actuation module can be of one of the following type: mechanical, pneumatic, hydraulic, electrical, electronical, optical, a combination thereof, etc. The one or more command controls operations of the at least one actuation module. The one or more command is transmitted over a communication network via the communication interface 130 of the controller 100. The processing appliances 400A and 400B may also comprise a processing unit for controlling the operations of the at least one actuation module based on the received one or more command.

Examples of processing appliances (implementing various functionalities) have been provided previously in reference to potatoes to fries processing chain and include the following. A sorting appliance capable of sorting objects (e.g. sorting potatoes), to eliminate objects which do not comply with given geometric characteristics (e.g. potatoes that are too big or too small). An example of command transmitted by the controller 100 to the sorting appliance is a command for modifying the given geometric characteristics (e.g. increase or decrease the size of the potatoes to eliminate). A cleaning appliance capable of cleaning objects (e.g. cleaning potatoes). An example of command transmitted by the controller 100 to the cleaning appliance is a command for increasing (or decreasing) a rate or a pressure of a flow of liquid used for the cleaning process. A cutting appliance capable of cutting objects (e.g. peeling or slicing potatoes). An example of command transmitted by the controller 100 to the cutting appliance is a command for increasing (or decreasing) a speed or an applied pressure of a blade used in the cutting process. A heating appliance capable of heating objects (e.g. cooking fries or drying cooked fries). An example of command transmitted by the controller 100 to the heating appliance is a command for increasing or decreasing the temperature of the heating process. Each of the aforementioned processing appliances comprises at least one actuation module for implementing its specific functionality (e.g. sorting, cleaning, cutting, heating, etc.), each actuation module being remotely controllable via commands transmitted by the controller 100. A person skilled in the art of would readily understand that other types of processing appliances may be controlled by the controller 100 according to the method 500 (which will be described in detail in the following).

Also represented in FIG. 4 is an information server 450. The information server 450 comprises a processing unit, memory, a communication interface, optionally a user interface, etc. (not represented in FIG. 4 for simplification purposes). The memory of the information server 450 stores additional data related to the product processed by the processing chain 10. The additional data are different from the data collected by the sensors 300. The additional data are provided by a user via the user interface of the information server 450. Alternatively or complementarily, the additional data are received from a remote computing device (e.g. located at a supplier) via the communication interface of the information server 450. The information server 450 can be located in a vicinity of the processing chain 10 or may be remotely located (e.g. in a cloud computing infrastructure). The information server 450 may implement a database for storing the additional data. The additional data are transmitted to the controller 100 via the communication interface of the information server 450, and are used for implementing the method 500. More than one information server 450 may be storing additional data related to the product processed by the processing chain 10, the additional data being used by the controller 100 for implementing the method 500. Optionally, the functionalities of the information server 450 are integrated to the controller 100 and the additional data are directly stored in the memory 120 of the controller 100 (after reception from a remote computing device via the communication interface 130 and/or from a user via the user interface 140). In this case, the remote computing device plays the role of the information server with respect to the controller 100.

Examples of additional data related to the product include a supplier of the product, a variety of the product (e.g. a variety of potatoes), a brix value (measure of sugar content) of the product, a pH level of the product (a measure of how acidic or basic the product is), longitude/latitude coordinates of the harvest location of the product, a harvest date of the product, an array of check points (longitude/latitude coordinates) while the product was in transit towards the food factory, an array of dates/corresponding measures of vibration of the product from harvest to manufacturing start, an array of dates/corresponding measures of temperature of the product from harvest to manufacturing start, an array of dates/corresponding measures of humidity level of the product from harvest to manufacturing start, etc.

Following are additional data which may be used as inputs: quality code measure of quality (numeric scale), average weight based on a sample of 50, temperature low during transport, temperature high during transport, percentage of products in sample that have growth cracks, percentage of products in sample that have dry rot, percentage of products in sample that have soft rot, percentage of products in sample that are misshapen, percentage of products in sample that have black holes, percentage of products in sample that have insect damage, percentage of products in sample that have porous holes, percentage of products in sample that have white rot, percentage of products in sample that have rodent damage, percentage of products in sample that have scabs, percentage of products in sample that have internal defects, etc.

The method 500 comprises the step 505 of executing the neural network training engine 211 (by the processing unit of the training server 200) to generate the predictive model. This step will be detailed later in the description and consists in training a neural network with a large sample of training data to generate the predictive model. The predictive model comprises the weights of the neural network, which are determined via this training process.

The method 500 comprises the step 510 of transmitting the predictive model to the controller 100, via the communication interface of the training server 200.

The method 500 comprises the step 515 of storing the predictive model in the memory 120 of the controller 100. The predictive model is received via the communication interface 130 of the controller 100, and stored in the memory 120 by the processing unit 110.

The method 500 comprises the step 520 of collecting data representative of characteristics of the product processed by the processing chain 10. Step 520 is performed by the control module 114 executed by the processing unit 110. At least some of the collected data are received via the communication interface 130 from the sensor(s) 300 monitoring operations of the processing chain 10. The data received from the sensor(s) 300 are (quasi) real time data, which may be different for each iteration of step 535. However, in some cases, these data may not evolve in (quasi) real time. Examples of such data have been provided previously in relation to the description of the sensors 300.

Optionally, some of the collected data representative of characteristics of the product are received via the communication interface 130 from one or more information server 450 as mentioned previously, and/or via the user interface 140. These data do not evolve in real time and can be stored in the memory 120 for a subsequent period of time once they are received. Thus, these data generally have the same value for a plurality of iterations of step 535. However, in some cases, these data may evolve in (quasi) real time. Examples of such data have been provided previously in relation to the description of the information server 450.

The same type of data may be collected via the sensors 300 or via the information server 450. For example, the average weight of the product entering the processing chain 10 (e.g. average weight of a potato) is calculated based on data collected by one or more weighting sensor. Alternatively, a value of the average weight of the product entering the processing chain 10 (e.g. average weight of a potato) is stored in the information server 450 and transmitted to the controller 10.

The method 500 comprises the step 525 of determining at least one product characteristic value based on the data collected at step 520. Step 525 is performed by the control module 114 executed by the processing unit 110.

The implementation of step 525 is adapted for each type of data collected at step 520. For a first given type of data collected at step 520, the determination of the product characteristic value simply consists in using the value collected at step 520 for the first given type of data. For a second given type of data collected at step 520, the determination of the product characteristic value consists in processing the value(s) collected at step 520 for the second given type of data to generate the corresponding product characteristic value.

For example, for a first type of product characteristic value (e.g. temperature of the products), a series of values is received from a sensor 300 over a given period of time and the processing unit 110 calculates an average of the series of values for the given period of time. The average value is calculated at step 525 and used as an input of the neural network at step 535.

For a second type of product characteristic value (e.g. weight of the products), a single value is received from a sensor 300 for a given period of time and the single value (e.g. an average weight of the products or a cumulative weights of the products directly determined by the sensor 300) is directly used as an input of the neural network at step 535 (no pre-processing is performed according to step 525).

With respect to the data collected from the information server 450, these data can generally be used directly as product characteristic values without further processing (e.g. the information server 450 directly stores the average weight of the products, the average humidity level of the products, the average number of defects of the products, etc.).

The method 500 comprises the optional step 530 of collecting additional data. Step 530 is performed by the control module 114 executed by the processing unit 110. The additional data are not directly related to the product processed by the processing chain 10.

As mentioned previously, an example of additional data includes at least one of a temperature/a humidity level/a lighting level, in the area where the processing chain 10 is operating. These additional data are received from dedicated sensors (different from the sensors 300) via the communication interface 130.

Another type of additional data includes at least one current operating parameter of the processing chain 10. For instance, the additional data include one or more current operating parameter of one or more processing appliance (e.g. 400A or 400B) of the processing chain 10. Current operating parameters may include for example a current sorting size for a sorting appliance, a current rate or pressure of a flow of liquid for a cleaning appliance, a current speed or applied pressure of a blade for a cutting appliance, a current operating temperature for a heating appliance, etc.

Operating parameters of a processing appliance may influence operations of another processing appliance. Thus, if the method 500 is performed for determining command(s) to be sent to the processing appliance 400A, the inputs may include current operating parameter(s) of the processing appliance 400A, and optionally also current operating parameter(s) of the processing appliance 400B.

Still another type of additional data includes a target yield. For example, a target yield is defined for the processing chain 10 and consists of a target quantity of product exiting the processing chain 10 (for example fries) divided by a given quantity of product having entered the processing chain 10 (for example raw potatoes) for producing the target quantity of product exiting the processing chain 10. For instance, the target yield corresponds to a target weight of product exiting the processing chain 10 over a given period of time (for example one minute or one hour) divided by a given weight of product having entered the processing chain 10 for producing the target weight of product exiting the processing chain 10. In another example, a target yield is defined for a given processing appliance (e.g. 400A or 400B) of the processing chain 10 and consists of a target quantity of product exiting the given processing appliance (for example unpeeled potatoes) divided by a given quantity of product having entered the given processing appliance (for example peeled potatoes) for producing the target quantity of product exiting the given processing appliance. The one or more target yield is received from a user via the user interface 140 or received from a remote computing device (for example a mobile device used by an operator of the processing chain 10 for piloting operations of the processing chain 10) via the communication interface 130. The target yield is an objective, and is not based on measurements performed by sensors 300. Other types of metrics than the weight of product may be used for assessing a yield (for example a ratio of a volume of product exiting and entering the processing chain 10).

Still another type of additional data includes a current yield. A current yield is determined based on measurements. For example, a current yield is defined for the processing chain 10 and consists of a current quantity of product exiting the processing chain 10 (for example weight of fries over a given period of time) divided by a corresponding quantity of product having entered the processing chain 10 (for example corresponding weight of raw potatoes used for producing the weight of fries) for producing the current quantity of product exiting the processing chain 10. In another example, a current yield is defined for a given processing appliance (e.g. 400A or 400B) of the processing chain 10 and consists of a current quantity of product exiting the given processing appliance (for example weight of unpeeled potatoes over a given period of time) divided by a corresponding quantity of product having entered the given processing appliance (for example corresponding weight of peeled potatoes used for producing the weight of unpeeled potatoes). The one or more current yield is calculated by the processing unit 110 based on measurements received via the communication interface 130 from sensors 300. Alternatively, the one or more current yield is directly received by the processing unit 110 via the communication interface 130 from a computing device, which calculated the one or more current yield based on the measurements transmitted by the sensors 300 (for example weight sensor).

Still another type of additional data includes a target quality metric. For example, a target quality metric is defined for the processing chain 10 and consists of a target value of a metric representative of the quality of product exiting the processing chain 10. In another example, a target quality metric is defined for a given processing appliance (e.g. 400A or 400B) of the processing chain 10 and consists of a target value of a metric representative of the quality of product exiting the given processing appliance. The one or more target quality metric is received from a user via the user interface 140 or received from a remote computing device (for example a mobile device used by an operator of the processing chain 10 for piloting operations of the processing chain 10) via the communication interface 130. The target quality metric is an objective, and is not based on measurements performed by sensors 300.

Examples of quality metrics defined for refined product exiting the processing chain 10 and/or a processing appliance (e.g. 400A) include a minimum or/and maximum average weight, a minimum or/and maximum average size, a maximum average number of defect, a maximum average size of a defect, a minimum or/and maximum average viscosity, a minimum or/and maximum average concentration of a compound in the product (e.g. brix), etc.

Still another type of additional data includes a current quality metric. A current quality metric is determined based on measurements. For example, a current quality metric is defined for the processing chain 10 and consists of a current value of a metric representative of the quality of product exiting the processing chain 10. In another example, a current quality metric is defined for a given processing appliance (e.g. 400A or 400B) of the processing chain 10 and consists of a current value of a metric representative of the quality of product exiting the given processing appliance. The one or more current quality metric is calculated by the processing unit 110 based on measurements received via the communication interface 130 from sensors 300. Alternatively, the one or more current quality metric is directly received by the processing unit 110 via the communication interface 130 from a computing device, which calculated the one or more current quality metric based on the measurements transmitted by the sensors 300. Examples of quality metrics have been described previously.

Still another type of additional data includes a target $CO_2$ footprint. For example, a target $CO_2$ footprint is defined for the processing chain 10 and consists of a target value of a metric representative of the $CO_2$ footprint of the processing chain 10. In another example, a target $CO_2$ footprint is defined for a given processing appliance (e.g. 400A or 400B) of the processing chain 10 and consists of a target value of a metric representative of the $CO_2$ footprint of the given processing appliance. The one or more target $CO_2$ footprint is received from a user via the user interface 140 or received from a remote computing device (e.g. a mobile device used by an operator of the processing chain 10 for piloting operations of the processing chain 10) via the communication interface 130. The target $CO_2$ footprint is an objective and is not based on measurements performed by sensors 300.

The calculation of a $CO_2$ footprint takes into consideration a plurality of contributions to the $CO_2$ footprint. These contributions include publicly available $CO_2$ footprint data related to operations of the processing chain 10, estimated $CO_2$ footprint data related to the production and/or transport of the inputs of processing chain 10 (for example growing potatoes and transporting the potatoes from the field to the food factory), estimated $CO_2$ footprint data related to operations of the processing appliances of the processing chain 10 (e.g. power consumption, water consumption, chemical inputs consumption, etc.), estimated $CO_2$ footprint of the packaging of the product exiting the processing chain 10, etc. In particular, the estimated $CO_2$ footprint data related to operations of the processing appliances of the processing chain 10 can be measured in (quasi) real time and adjusted by modifying operating conditions of the processing appliances of the processing chain 10.

Still another type of additional data includes a current $CO_2$ footprint. A current $CO_2$ footprint is determined based on measurements. For example, a current $CO_2$ footprint is defined for the processing chain 10 and consists of a current value of a metric representative of the $CO_2$ footprint of the processing chain 10. In another example, a current $CO_2$ footprint is defined for a given processing appliance (e.g. 400A or 400B) of the processing chain 10 and consists of a current value of a metric representative of the $CO_2$ footprint of the given processing appliance. The one or more current $CO_2$ footprint is calculated by the processing unit 110 based on raw data received via the communication interface 130 (e.g. data representative of operating conditions of processing appliances, such as power consumption). Alternatively, the one or more current $CO_2$ footprint is directly received by the processing unit 110 via the communication interface 130 from a computing device, which calculated the one or more current $CO_2$ footprint based on raw data (e.g. data representative of operating conditions of processing appliances, such as power consumption). Alternatively, an estimation of the current $CO_2$ footprint is provided by a user via the user interface 140. Examples of $CO_2$ footprint contributions have been described previously.

The method 500 comprises the step 535 of executing the neural network inference engine 112 (by the processing unit 110). The neural network inference engine 112 implements a neural network using the predictive model (stored in memory 120 at step 515 and comprising the weights of the neural network) for generating one or more output based on inputs.

The one or more output comprises one or more command for controlling at least processing appliance. For example, the one or more output comprises at least one command for controlling a single processing appliance (e.g. 400A). In another example, the one or more output comprises at least one command for controlling two or more processing appliances (e.g. 400A and 400B). In the second example, a given command is targeted to a single processing appliance (e.g. only 400A). Alternatively, the same given command is targeted to several processing appliances (e.g. 400A and 400B). Examples of such commands have been described previously in the context of a processing chain transforming potatoes into fries.

The inputs comprise the at least one product characteristic value determined at step 525. If the optional step 530 is performed, then the inputs further comprise the additional data collected at step 530.

In a particular implementation, instead of using a single value for a given type of input of the neural network, a series of consecutive values is used as inputs. For example, a series of temperatures of the products is received over a period of time from a temperature sensor 300 at step 520. Instead of calculating an average temperature at step 525 based on the series of temperatures received at step 525, the series of temperatures is directly used as inputs of the neural network at step 535. If the series comprises N values (e.g. 5), in the first case, the neural network receives one input consisting of the average of the N values; and in the second case, the neural network receives N inputs consisting of the N values of the series. One or more types of inputs of the neural network may use a series of values for the inputs instead of a single value (e.g. an average of the series of values).

The neural network may also use convolution layer(s) and optionally pooling layer(s) following the convolution layer(s). For example, if a given type of input consists of a series of values, a one-dimension convolution is applied to the series of values before further processing by the neural network. In another example, if several given types of input consist of several series of values, a two-dimension convolution is applied to the several series of values before further processing by the neural network.

The method 500 comprises the step 540 of transmitting the one or more command to the respective processing appliance(s) (e.g. 400A and optionally 400B) via the communication interface 130. Step 540 is performed by the control module 114 executed by the processing unit 110

The method 500 comprises the step 545 of applying by the respective controlled appliance(s) (e.g. 400A and optionally 400B) the one or more command received from the controller 100.

Steps 525, optionally 530, 535 and 540 are repeated each time new data are collected at step 520. However, configurable thresholds may be used for the data received at step 520, so that a change in the value of a given type of data is not taken into consideration (steps 525, optionally 530, 535 and 540 are not performed) as long as the change remains within the boundaries of the corresponding threshold(s). For example, if the type of data is a product temperature measured by a sensor 300, the threshold can be an increment/decrease of one degree Celsius between a currently received product temperature and a previously received product temperature. Alternatively or complementarily, configurable thresholds are defined for the product characteristic value(s) determined at step 525, so that a change in a value of a given characteristic value may not be taken into consideration (steps 535 and 540 are not performed) based on corresponding configurable threshold(s).

Following is a description of the training phase, which results in the generation of the predictive model. During the training phase, the neural network training engine 211 is trained with a plurality of inputs and a corresponding plurality of outputs. Each input comprises product characteristic value(s) and optionally additional data as mentioned previously, and each corresponding output comprises one or more command for controlling processing appliance(s) (e.g. 400A).

As is well known in the art of neural network, during the training phase, the neural network implemented by the neural network training engine 211 adjusts its weights. Furthermore, during the training phase, the number of layers of the neural network and the number of nodes per layer can be adjusted to improve the accuracy of the model. At the end of the training phase, the predictive model generated by the neural network training engine 211 includes the number of layers, the number of nodes per layer, and the weights.

The inputs and outputs for the training phase of the neural network can be collected through an experimental process. For example, a plurality of combinations of product characteristic values are tested. For each combination, a plurality of command(s) for controlling the processing appliance(s) are tested, and the most adequate command(s) is determined based on criteria for evaluating the performance of the processing chain 10. In addition to the product characteristic values, each combination may include additional parameters representative of the current state of the processing chain 10 and/or of a given processing appliance (e.g. 400A) of the processing chain 10. Such additional parameters have been mentioned previously and include current operating parameters of a given processing appliance, a current yield, a current quality metric, a current $CO_2$ footprint, etc. One example of evaluation criterium is a target yield for the whole processing chain 10 and/or a target yield for a given processing appliance (e.g. 400A). Another example of evaluation criterium is a target quality metric defined for the whole processing chain 10 and/or a target quality metric defined for a given processing appliance (e.g. 400A). Another example of evaluation criterium is a maximum power consumption for operating the processing chain 10. Another example of evaluation criterium is a maximum duration for performing a transformation of a raw or pre-processed product into a refined product through the processing chain. Alternatively or complementary, the maximum duration is defined for performing the operations of a given processing appliance (e.g. 400A). Another example of evaluation criterium is stress imposed on components of one or more processing appliance (e.g. 400A), for instance mechanical stress, heating stress, etc. The neural network training engine 211 is trained with the combination of inputs (product characteristic values and optional additional parameters) and corresponding output(s) (one or more corresponding most adequate command) which meet the evaluation criteria, or at least provide the best results with respect to meeting the evaluation criteria. The most adequate command(s) may also be determined for various values of a target yield, a target quality metric or a target carbon footprint, which are also respectively used as input for the training of the neural network. For example, the most adequate command(s) are determined for a target yield varying from 70 to 90 percent by increments of approximatively 1 percent. In this case, the target yield is also used as an input for the training of the neural network.

In some cases, the training phase cannot be performed via an experimental process, because it is too long, too costly or too complicated to implement. In this case, during standard operations of the processing chain 10, all the data necessary for the training are collected. Then, the training is performed in a manner similar to the one previously described for the experimental process, except that the training is based on the data collected during the standard operations of the processing chain 10.

Various techniques well known in the art of neural networks are used for performing (and improving) the generation of the predictive model, such as forward and backward propagation, usage of bias in addition to the weights (bias and weights are generally collectively referred to as weights in the neural network terminology), reinforcement training, etc.

During the operational phase, the neural network inference engine 112 uses the predictive model (e.g. the values of the weights) determined during the training phase to infer output(s) (e.g. one or more command for controlling the processing appliance 400A) based on inputs (e.g. product characteristic values corresponding to data collected by the sensors 300) as is well known in the art.

Figure 6:
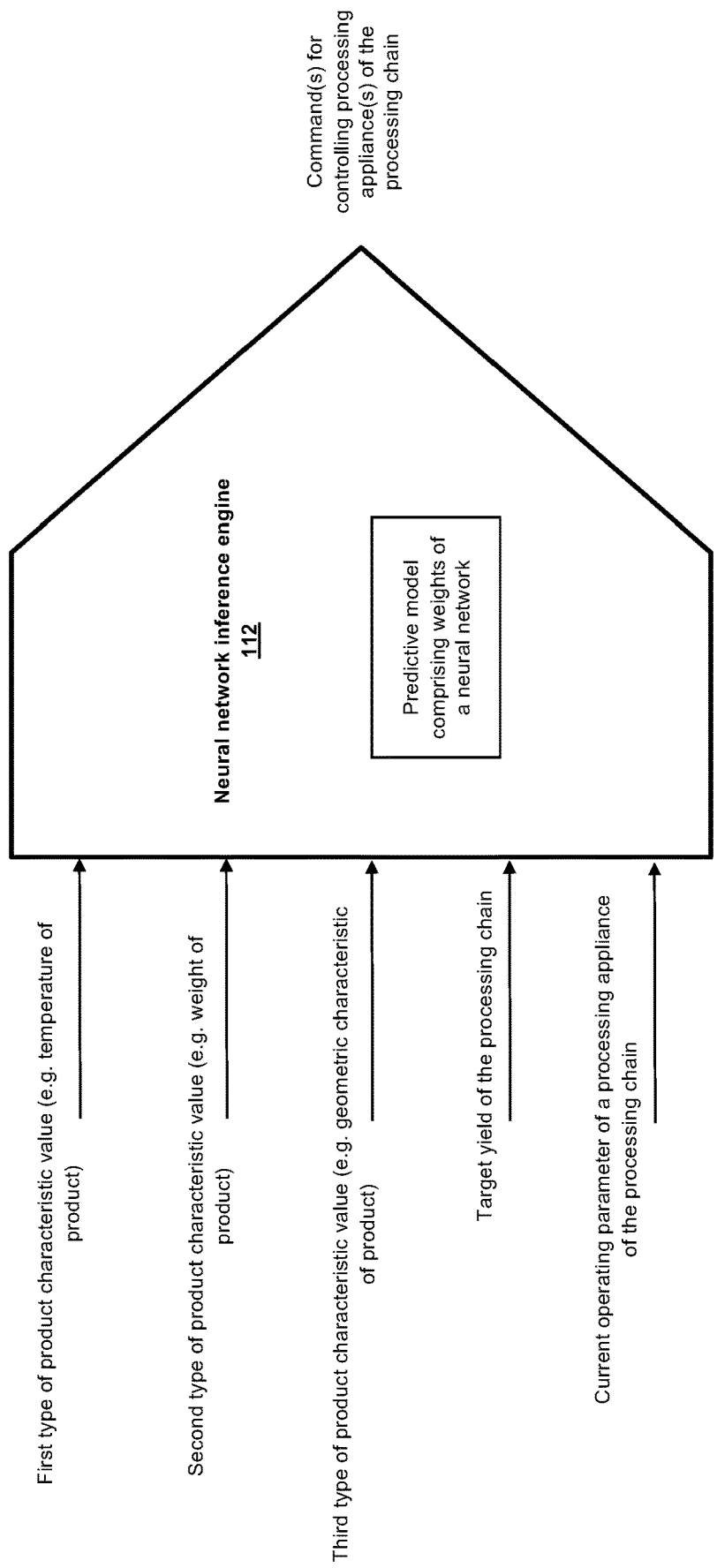
FIG. 6 is a schematic representation of a neural network inference engine executed by the controller of FIGS. 2, 3 and 4 when implementing the method of FIG. 5.

Reference is now made to FIGS. 4, 5 and 6, where FIG. 6 illustrates the neural network inference engine 112 with its inputs and its output(s). FIG. 6 corresponds to the neural network inference engine 112 represented in FIG. 4 and executed at step 535 of the method 500 represented in FIG. 5. The inputs represented in FIG. 6 are for illustration purposes only, and correspond to an exemplary combination of the previously described types of inputs.

Figure 7:
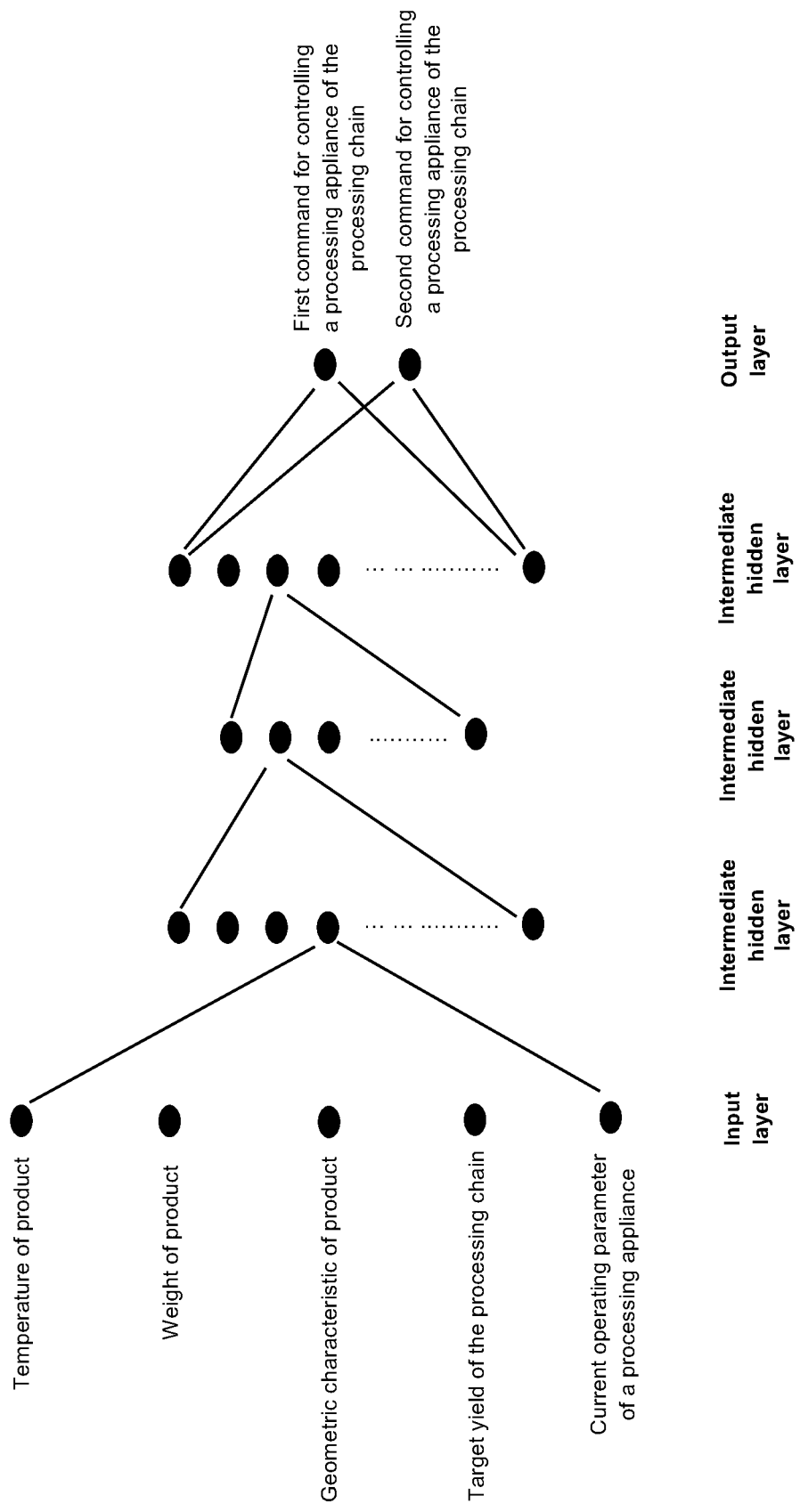
FIG. 7 is a detailed representation of a neural network implemented by the neural network inference engine of FIG. 7.

Reference is now made concurrently to FIGS. 5, 6 and 7, where FIG. 7 is a detailed representation of the neural network implemented by the neural network inference engine 112 schematically represented in FIG. 6. The neural network includes an input layer with five neurons for receiving inputs consisting of a temperature of the product, a weight of the product, a geometric characteristic of the product, a target yield of the processing chain 10 and a current operating parameter of a processing appliance (e.g. 400A) of the processing chain 10. The neural network includes an output layer with two neurons for outputting two outputs consisting of a first command for controlling a processing appliance (e.g. 400A) of the processing chain 10 and a second command for controlling a processing appliance (e.g. 400A or 400B) of the processing chain 10. The number of neurons of the input layer, the inputs, the number of neurons of the output layer and the outputs represented in FIG. 7 are for illustration purposes, and can be adapted to support all the use cases described in relation to the method 500. The neural network includes three intermediate hidden layers between the input layer and the output layer. All the layers are fully connected. A layer L being fully connected means that each neuron of layer L receives inputs from every neurons of layer L−1, and applies respective weights to the received inputs. By default, the output layer is fully connected to the last hidden layer. The number of intermediate hidden layers is an integer greater or equal than 1 (FIG. 7 represents three intermediate hidden layers for illustration purposes only). The number of neurons in each intermediate hidden layer may vary. During the training phase of the neural network, the number of intermediate hidden layers and the number of neurons for each intermediate hidden layer are selected, and may be adapted experimentally. The generation of the outputs based on the inputs using weights allocated to the neurons of the neural network is well known in the art. The architecture of the neural network, where each neuron of a layer (except for the first layer) is connected to all the neurons of the previous layer is also well known in the art.

Inference of Predicted Yield

Figure 8:
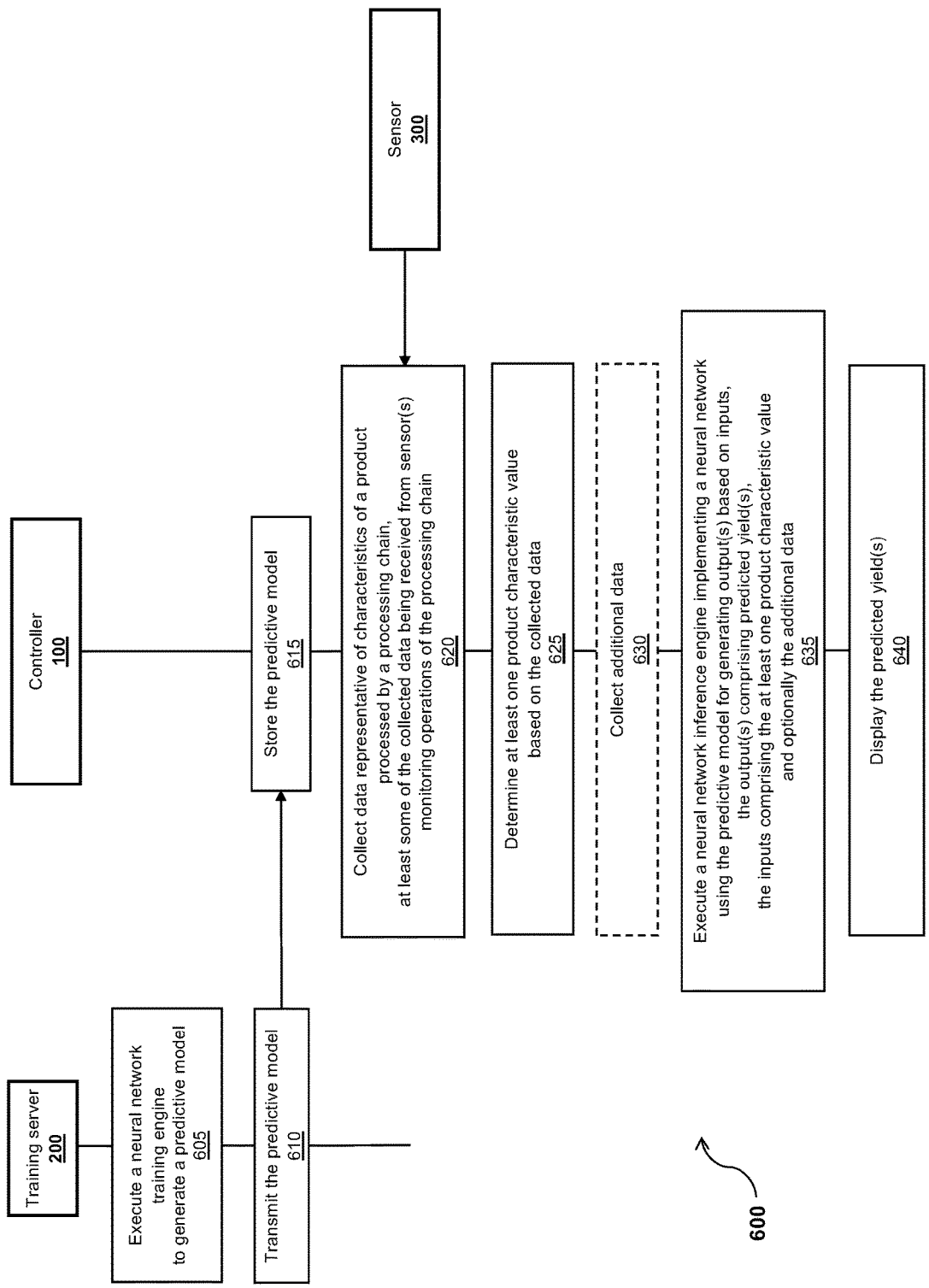
FIG. 8 illustrates a method using a neural network to infer a predicted yield for the processing chain of FIGS. 2 and 3.

Reference is now made concurrently to FIGS. 1, 2, 3, 4, 5 and 8. FIG. 8 represents a method 600 using a neural network for inferring predicted yield(s).

In the following, the neural network training engine 211 and the neural network inference engine 112 are used for respectively generating and using a predictive model capable of generating output(s) comprising the predicted yield(s) based on inputs. As mentioned previously, the predicted yield is defined for the processing chain 10 or for a given processing appliance (e.g. 400A) of the processing chain 10. The output(s) may comprise one or more predicted yield (e.g. one for the processing chain 10 and/or one for the processing appliance 400A). At least some of the inputs are similar to the inputs used in the context of method 500 represented in FIG. 5.

At least some of the steps of the method 600 are implemented by the controller 100, making use of the neural network to infer the predicted yield(s).

A dedicated computer program has instructions for implementing at least some of the steps of the method 600. The instructions are comprised in a non-transitory computer program product (e.g. the memory 120) of the controller 100. The instructions, when executed by the processing unit 110 of the controller 100, provide for making use of a neural network to infer predicted yield(s). The instructions are deliverable to the controller 100 via an electronically-readable media such as a storage media (e.g. CD-ROM, USB key, etc.), or via communication links (e.g. via a communication network through the communication interface 130).

The dedicated computer program product executed by the processing unit 110 comprises the neural network inference engine 112 and the control module 114.

The method 600 comprises the step 605 of executing the neural network training engine 211 (by the processing unit of the training server 200) to generate the predictive model. This step consists in training a neural network with a large sample of training data to generate the predictive model. The predictive model comprises the weights of the neural network, which are determined via this training process. Step 605 is similar to step 505 of the method 500. However, the predictive models generated at steps 605 and 505 are different.

The method 600 comprises the step 610 of transmitting the predictive model to the controller 100, via the communication interface of the training server 200

The method 600 comprises the step 615 of storing the predictive model in the memory 120 of the controller 100. The predictive model is received via the communication interface 130 of the controller 100, and stored in the memory 120 by the processing unit 110.

The method 600 comprises the step 620 of collecting data representative of characteristics of the product processed by the processing chain 10. Step 620 is performed by the control module 114 executed by the processing unit 110. Step 620 is similar to step 520 of the method 500. At least some of the collected data are received via the communication interface 130 from the sensor(s) 300 monitoring operations of the processing chain 10. The data received from the sensor(s) 300 are (quasi) real time data, which may be different for each iteration of step 635. However, in some cases, these data may not evolve in (quasi) real time. Examples of such data have been provided previously in relation to the description of the sensors 300.

Optionally, some of the collected data representative of characteristics of the product are received via the communication interface 130 from one or more information server 450 as mentioned previously, and/or via the user interface 140. These data do not evolve in real time and can be stored in the memory 120 for a subsequent period of time once they are received. Thus, these data generally have the same value for a plurality of iterations of step 635. However, in some cases, these data may evolve in (quasi) real time. Examples of such data have been provided previously in relation to the description of the information server 450.

The method 600 comprises the step 625 of determining at least one product characteristic value based on the data collected at step 620. Step 625 is performed by the control module 114 executed by the processing unit 110. Step 625 is similar to step 525 of the method 500.

As mentioned previously in relation to step 525 of the method 500, the implementation of step 625 is adapted for each type of data collected at step 620. For a first given type of data collected at step 620, the determination of the product characteristic value simply consists in using the value collected at step 620 for the first given type of data. For a second given type of data collected at step 620, the determination of the product characteristic value consists in processing the value(s) collected at step 620 for the second given type of data to generate the corresponding product characteristic value. Furthermore, with respect to the data collected from the information server 450, these data can generally be used directly as product characteristic values without further processing.

The method 600 comprises the optional step 630 of collecting additional data. Step 630 is performed by the control module 114 executed by the processing unit 110. The additional data are not directly related to the product processed by the processing chain 10. Step 630 is similar to step 530 of the method 500.

As mentioned previously, an example of additional data includes at least one of a temperature/a humidity level/a lighting level, in the area where the processing chain 10 is operating. These additional data are received from dedicated sensors (different from the sensors 300) via the communication interface 130.

Another type of additional data includes at least one current operating parameter of the processing chain 10. For instance, the additional data include one or more current operating parameter of one or more processing appliance (e.g. 400A or 400B) of the processing chain 10. Examples of operating parameters have been provided previously.

Still another type of additional data includes one or more current yield. Current yields have been described previously. A current yield can be defined for the processing chain 10 or for a given processing appliance (e.g. 400A or 400B) of the processing chain 10.

Still another type of additional data includes one or more target quality metric. Target quality metrics have been described previously. A target quality metric can be defined for the processing chain 10 or for a given processing appliance (e.g. 400A or 400B) of the processing chain 10.

Still another type of additional data includes one or more current quality metric. Current quality metrics have been described previously. A current quality metric can be defined for the processing chain 10 or for a given processing appliance (e.g. 400A or 400B) of the processing chain 10.

Still another type of additional data includes one or more target $CO_2$ footprint. Target $CO_2$ footprints have been described previously. A target $CO_2$ footprint can be defined for the processing chain 10 or for a given processing appliance (e.g. 400A or 400B) of the processing chain 10.

Still another type of additional data includes one or more current $CO_2$ footprint. Current $CO_2$ footprints have been described previously. A current $CO_2$ footprint can be defined for the processing chain 10 or for a given processing appliance (e.g. 400A or 400B) of the processing chain 10.

The method 600 comprises the step 635 of executing the neural network inference engine 112 (by the processing unit 110). The neural network inference engine 112 implements a neural network using the predictive model (stored in memory 120 at step 615 and comprising the weights of the neural network) for generating one or more output based on inputs.

The one or more output comprises one or more predicted yield. Each predicted yield is a prediction of a value of a yield when the processing chain 10 is operating in conditions corresponding to the inputs of the neural network. As mentioned previously, a predicted yield can be defined for the processing chain 10 or for a given processing appliance (e.g. 400A or 400B) of the processing chain 10.

The inputs comprise the at least one product characteristic value determined at step 625. If the optional step 630 is performed, then the inputs further comprise the additional data collected at step 630.

As mentioned previously, instead of using a single value for a given type of input of the neural network, a series of consecutive values may be used as inputs. The neural network may also use convolution layer(s) and optionally pooling layer(s) following the convolution layer(s). For example, a one-dimension convolution is applied to a series of values corresponding to a given type of input and a two-dimension convolution is applied to several series of values corresponding to several types of input.

The method 600 comprises the step 640 of displaying the predicted yield(s) on the display 150 of the controller 100. Step 640 is performed by the control module 114 executed by the processing unit 110. Additionally or complementarily, the one or more predicted yield is transmitted to one or more computing device via the communication interface 130. Still other types of processing may be applied to the predicted yield(s) generated at step 635.

Steps 625, optionally 630, 635 and 640 are repeated each time new data are collected at step 620. As mentioned previously, configurable thresholds may be used for the data received at step 620, so that a change in the value of a given type of data is not taken into consideration (steps 625, optionally 630, 635 and 640 are not performed) as long as the change remains within the boundaries of the corresponding threshold(s).

The training phase, which results in the generation of the predictive model, is similar to the training phase described in the context of the method 500. During the training phase, the neural network training engine 211 is trained with a plurality of inputs and a corresponding plurality of outputs. Each input comprises product characteristic value(s) and optionally additional data as mentioned previously, and each corresponding output comprises predicted yield(s).

As is well known in the art of neural network, during the training phase, the neural network implemented by the neural network training engine 211 adjusts its weights. Furthermore, during the training phase, the number of layers of the neural network and the number of nodes per layer can be adjusted to improve the accuracy of the model. At the end of the training phase, the predictive model generated by the neural network training engine 211 includes the number of layers, the number of nodes per layer, and the weights.

As mentioned previously, the inputs and outputs for the training phase of the neural network can be collected through an experimental process. For example, a plurality of combinations of product characteristic values are tested. For each combination, one or more corresponding yield is determined. In addition to the product characteristic values, each combination may include additional parameters representative of the current state of the processing chain 10 and/or of a given processing appliance (e.g. 400A) of the processing chain 10. Such additional parameters have been mentioned previously and include current operating parameters of a given processing appliance, a current yield, a current quality metric, a current $CO_2$ footprint, etc. The neural network training engine 211 is trained with the combination of inputs (product characteristic values and optional additional parameters) and corresponding output(s) (one or more corresponding determined yield). The yield(s) corresponding to the aforementioned combinations of inputs may also be determined for various values of a target quality metric or a target carbon footprint, which are also respectively used as input for the training of the neural network. For example, the yields(s) are determined for a target quality metric expressed as a ratio varying from 90 to 100 percent by increments of approximatively 0.5 percent. In this case, the target quality metric is also used as an input for the training of the neural network.

Figure 9:
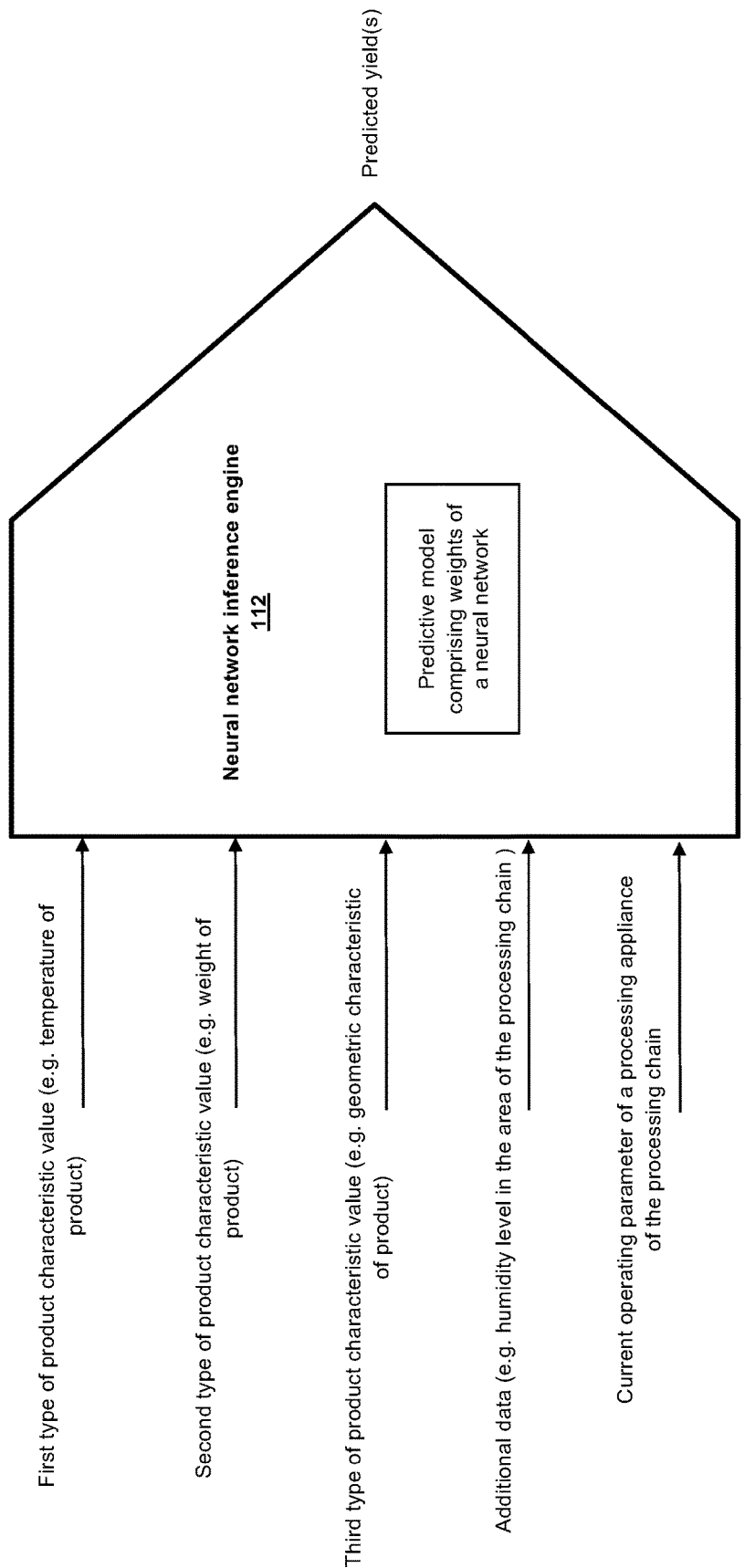
FIG. 9 is a schematic representation of a neural network inference engine executed by the controller of FIGS. 2, 3 and 4 when implementing the method of FIG. 8.

Reference is now made to FIGS. 4, 8 and 9, where FIG. 9 illustrates the neural network inference engine 112 with its inputs and its output(s). FIG. 9 corresponds to the neural network inference engine 112 represented in FIG. 4 and executed at step 635 of the method 600 represented in FIG. 8. The inputs represented in FIG. 9 are for illustration purposes only, and correspond to one exemplary combination of the previously described types of inputs.

Figure 10:
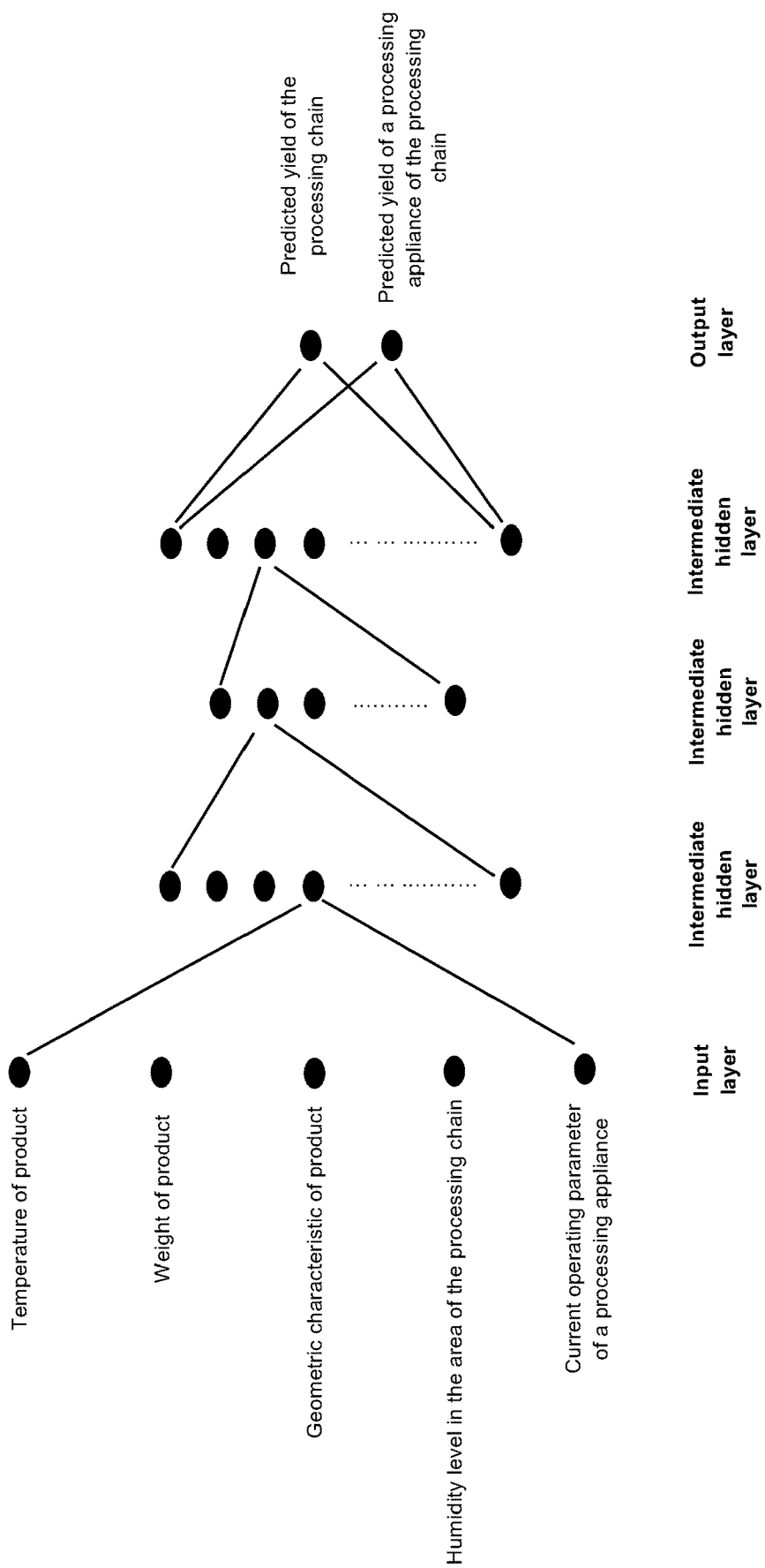
FIG. 10 is a detailed representation of a neural network implemented by the neural network inference engine of FIG. 9.

Reference is now made concurrently to FIGS. 8, 9 and 10, where FIG. 10 is a detailed representation of the neural network implemented by the neural network inference engine 112 schematically represented in FIG. 9. The neural network includes an input layer with five neurons for receiving inputs consisting of a temperature of the product, a weight of the product, a geometric characteristic of the product, a humidity level in the area of the processing chain 10 and a current operating parameter of a processing appliance (e.g. 400A) of the processing chain 10. The neural network includes an output layer with two neurons for outputting two outputs consisting of a predicted yield of the processing chain 10 and a predicted yield of a processing appliance (e.g. 400A) of the processing chain 10. The number of neurons of the input layer, the inputs, the number of neurons of the output layer and the outputs represented in FIG. 10 are for illustration purposes, and can be adapted to support all the use cases described in relation to the method 600. The neural network illustrated in FIG. 10 includes three intermediate hidden layers (for illustration purposes only) between the input layer and the output layer, and all the layers are fully connected. The number of neurons in each intermediate hidden layer may vary.

Inference of Predicted Quality Metric

Reference is now made concurrently to FIGS. 1, 2, 3, 4, 5 and 9. FIG. 9 represents a method 700 using a neural network for inferring predicted quality metric(s).

In the following, the neural network training engine 211 and the neural network inference engine 112 are used for respectively generating and using a predictive model capable of generating output(s) comprising the predicted quality metric(s) based on inputs. As mentioned previously, the predicted quality metric is defined for the processing chain 10 or for a given processing appliance (e.g. 400A) of the processing chain 10. The output(s) may comprise one or more predicted quality metric (e.g. one for the processing chain 10 and/or one for the processing appliance 400A). At least some of the inputs are similar to the inputs used in the context of method 500 represented in FIG. 5.

At least some of the steps of the method 700 are implemented by the controller 100, making use of the neural network to infer the predicted quality metric(s).

A dedicated computer program has instructions for implementing at least some of the steps of the method 700. The instructions are comprised in a non-transitory computer program product (e.g. the memory 120) of the controller 100. The instructions, when executed by the processing unit 110 of the controller 100, provide for making use of a neural network to infer predicted quality metric(s). The instructions are deliverable to the controller 100 via an electronically-readable media such as a storage media (e.g. CD-ROM, USB key, etc.), or via communication links (e.g. via a communication network through the communication interface 130).

The dedicated computer program product executed by the processing unit 110 comprises the neural network inference engine 112 and the control module 114.

The method 700 comprises the step 705 of executing the neural network training engine 211 (by the processing unit of the training server 200) to generate the predictive model. This step consists in training a neural network with a large sample of training data to generate the predictive model. The predictive model comprises the weights of the neural network, which are determined via this training process. Step 705 is similar to step 505 of the method 500. However, the predictive models generated at steps 705 and 505 are different.

The method 700 comprises the step 710 of transmitting the predictive model to the controller 100, via the communication interface of the training server 200.

The method 700 comprises the step 715 of storing the predictive model in the memory 120 of the controller 100. The predictive model is received via the communication interface 130 of the controller 100, and stored in the memory 120 by the processing unit 110.

The method 700 comprises the step 720 of collecting data representative of characteristics of the product processed by the processing chain 10. Step 720 is performed by the control module 114 executed by the processing unit 110. Step 720 is similar to step 520 of the method 500. At least some of the collected data are received via the communication interface 130 from the sensor(s) 300 monitoring operations of the processing chain 10. The data received from the sensor(s) 300 are (quasi) real time data, which may be different for each iteration of step 735. However, in some cases, these data may not evolve in (quasi) real time. Examples of such data have been provided previously in relation to the description of the sensors 300.

Optionally, some of the collected data representative of characteristics of the product are received via the communication interface 130 from one or more information server 450 as mentioned previously, and/or via the user interface 140. These data do not evolve in real time and can be stored in the memory 120 for a subsequent period of time once they are received. Thus, these data generally have the same value for a plurality of iterations of step 735. However, in some cases, these data may evolve in (quasi) real time. Examples of such data have been provided previously in relation to the description of the information server 450.

The method 700 comprises the step 725 of determining at least one product characteristic value based on the data collected at step 720. Step 725 is performed by the control module 114 executed by the processing unit 110. Step 725 is similar to step 525 of the method 500.

As mentioned previously in relation to step 525 of the method 500, the implementation of step 725 is adapted for each type of data collected at step 720. For a first given type of data collected at step 720, the determination of the product characteristic value simply consists in using the value collected at step 720 for the first given type of data. For a second given type of data collected at step 720, the determination of the product characteristic value consists in processing the value(s) collected at step 720 for the second given type of data to generate the corresponding product characteristic value. Furthermore, with respect to the data collected from the information server 450, these data can generally be used directly as product characteristic values without further processing.

The method 700 comprises the optional step 730 of collecting additional data. Step 730 is performed by the control module 114 executed by the processing unit 110. The additional data are not directly related to the product processed by the processing chain 10. Step 730 is similar to step 530 of the method 500.

As mentioned previously, an example of additional data includes at least one of a temperature/a humidity level/a lighting level, in the area where the processing chain 10 is operating. These additional data are received from dedicated sensors (different from the sensors 300) via the communication interface 130.

Another type of additional data includes at least one current operating parameter of the processing chain 10. For instance, the additional data include one or more current operating parameter of one or more processing appliance (e.g. 400A or 400B) of the processing chain 10. Examples of operating parameters have been provided previously.

Still another type of additional data includes one or more target yield. Target yields have been described previously. A target yield can be defined for the processing chain 10 or for a given processing appliance (e.g. 400A or 400B) of the processing chain 10.

Still another type of additional data includes one or more current yield. Current yields have been described previously. A current yield can be defined for the processing chain 10 or for a given processing appliance (e.g. 400A or 400B) of the processing chain 10.

Still another type of additional data includes one or more current quality metric. Current quality metrics have been described previously. A current quality metric can be defined for the processing chain 10 or for a given processing appliance (e.g. 400A or 400B) of the processing chain 10.

Still another type of additional data includes one or more target $CO_2$ footprint. Target $CO_2$ footprints have been described previously. A target $CO_2$ footprint can be defined for the processing chain 10 or for a given processing appliance (e.g. 400A or 400B) of the processing chain 10.

Still another type of additional data includes one or more current $CO_2$ footprint. Current $CO_2$ footprints have been described previously. A current $CO_2$ footprint can be defined for the processing chain 10 or for a given processing appliance (e.g. 400A or 400B) of the processing chain 10.

The method 700 comprises the step 735 of executing the neural network inference engine 112 (by the processing unit 110). The neural network inference engine 112 implements a neural network using the predictive model (stored in memory 120 at step 615 and comprising the weights of the neural network) for generating one or more output based on inputs.

The one or more output comprises one or more predicted quality metric. Each predicted quality metric is a prediction of a value of a quality metric when the processing chain 10 is operating in conditions corresponding to the inputs of the neural network. As mentioned previously, a predicted quality metric can be defined for the processing chain 10 or for a given processing appliance (e.g. 400A or 400B) of the processing chain 10. Examples of quality metrics have been described previously.

The inputs comprise the at least one product characteristic value determined at step 725. If the optional step 730 is performed, then the inputs further comprise the additional data collected at step 730.

As mentioned previously, instead of using a single value for a given type of input of the neural network, a series of consecutive values may be used as inputs. The neural network may also use convolution layer(s) and optionally pooling layer(s) following the convolution layer(s). For example, a one-dimension convolution is applied to a series of values corresponding to a given type of input and a two-dimension convolution is applied to several series of values corresponding to several types of input.

The method 700 comprises the step 740 of displaying the predicted quality metric(s) on the display 150 of the controller 100. Step 740 is performed by the control module 114 executed by the processing unit 110. Additionally or complementarily, the one or more predicted quality metric is transmitted to one or more computing device via the communication interface 130. Still other types of processing may be applied to the predicted quality metric(s) generated at step 735.

Steps 725, optionally 730, 735 and 740 are repeated each time new data are collected at step 720. As mentioned previously, configurable thresholds may be used for the data received at step 720, so that a change in the value of a given type of data is not taken into consideration (steps 725, optionally 730, 735 and 740 are not performed) as long as the change remains within the boundaries of the corresponding threshold(s).

The training phase, which results in the generation of the predictive model, is similar to the training phase described in the context of the method 500. During the training phase, the neural network training engine 211 is trained with a plurality of inputs and a corresponding plurality of outputs. Each input comprises product characteristic value(s) and optionally additional data as mentioned previously, and each corresponding output comprises predicted quality metric(s).

As is well known in the art of neural network, during the training phase, the neural network implemented by the neural network training engine 211 adjusts its weights. Furthermore, during the training phase, the number of layers of the neural network and the number of nodes per layer can be adjusted to improve the accuracy of the model. At the end of the training phase, the predictive model generated by the neural network training engine 211 includes the number of layers, the number of nodes per layer, and the weights.

As mentioned previously, the inputs and outputs for the training phase of the neural network can be collected through an experimental process. For example, a plurality of combinations of product characteristic values are tested. For each combination, one or more corresponding quality metric is determined. In addition to the product characteristic values, each combination may include additional parameters representative of the current state of the processing chain 10 and/or of a given processing appliance (e.g. 400A) of the processing chain 10. Such additional parameters have been mentioned previously and include current operating parameters of a given processing appliance, a current yield, a current quality metric, a current $CO_2$ footprint, etc. The neural network training engine 211 is trained with the combination of inputs (product characteristic values and optional additional parameters) and corresponding output(s) (one or more corresponding determined quality metric). The quality metric(s) corresponding to the aforementioned combinations of inputs may also be determined for various values of a target yield or a target carbon footprint, which are also respectively used as input for the training of the neural network. For example, the quality metrics are determined for a target yield varying from 70 to 90 percent by increments of approximatively 1 percent. In this case, the target yield is also used as an input for the training of the neural network.

Figure 11:
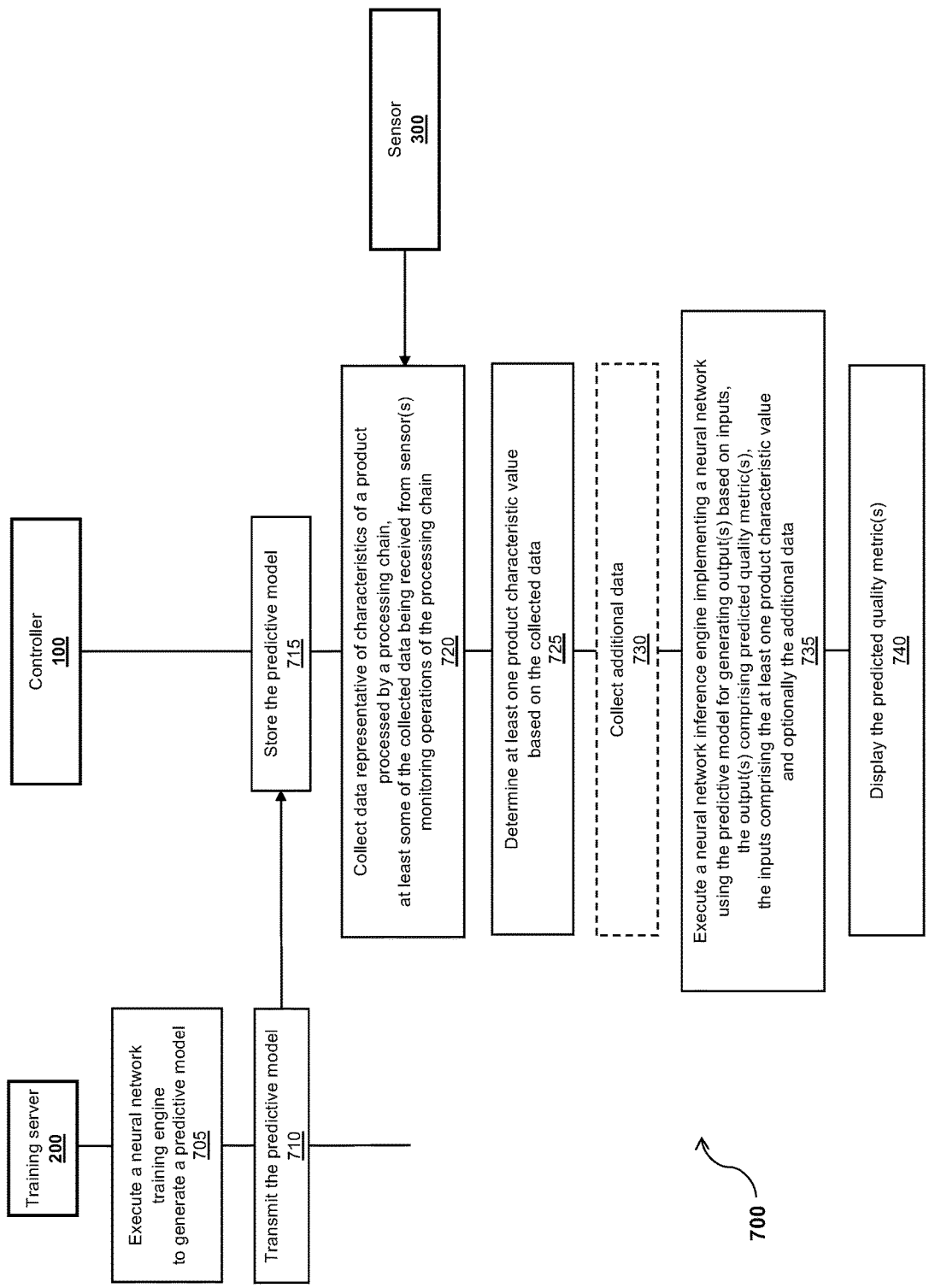
FIG. 11 illustrates a method using a neural network to infer a predicted quality metric for the processing chain of FIGS. 2 and 3.
Figure 12:
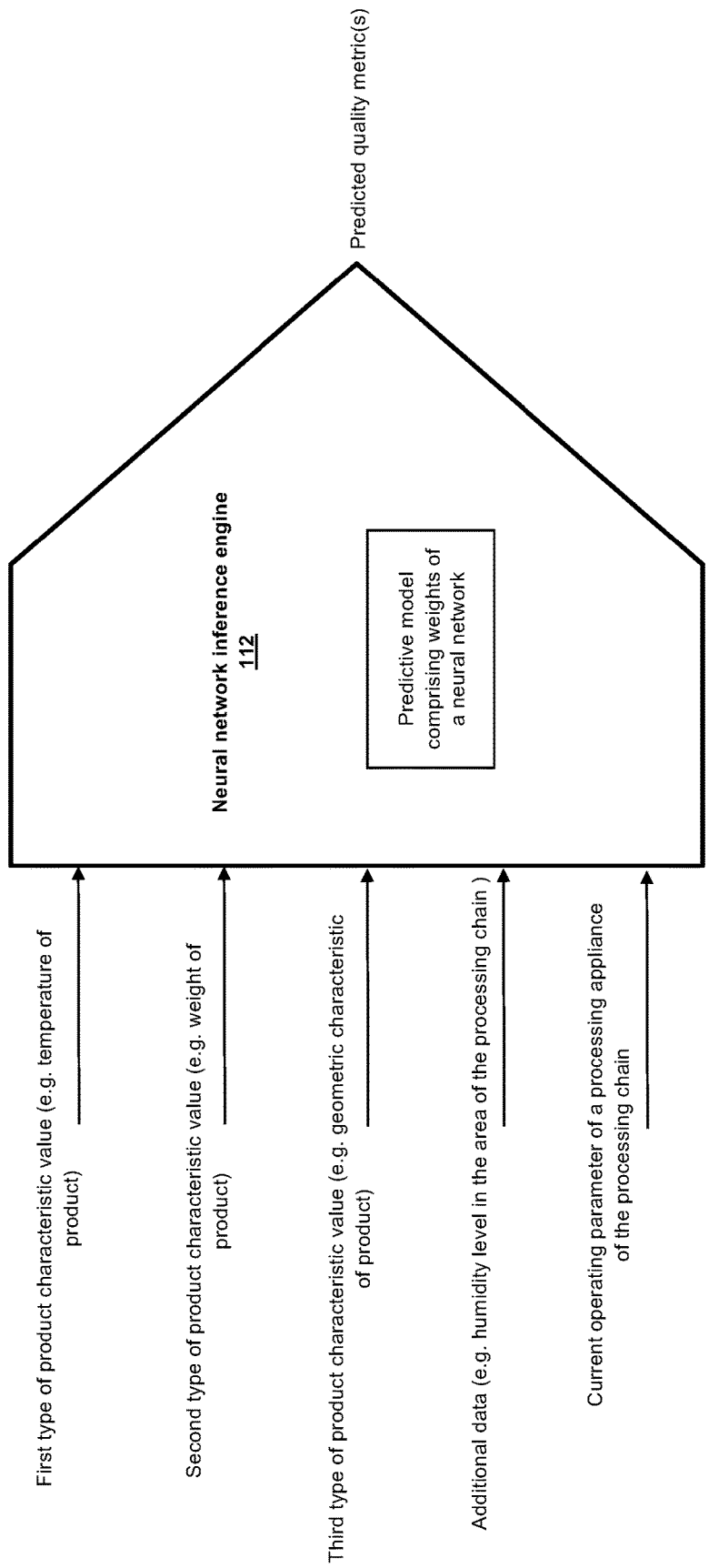
FIG. 12 is a schematic representation of a neural network inference engine executed by the controller of FIGS. 2, 3 and 4 when implementing the method of FIG. 11.

Reference is now made to FIGS. 4, 11 and 12, where FIG. 12 illustrates the neural network inference engine 112 with its inputs and its output(s). FIG. 12 corresponds to the neural network inference engine 112 represented in FIG. 4 and executed at step 735 of the method 700 represented in FIG. 11. The inputs represented in FIG. 12 are for illustration purposes only, and correspond to one exemplary combination of the previously described types of inputs.

Figure 13:
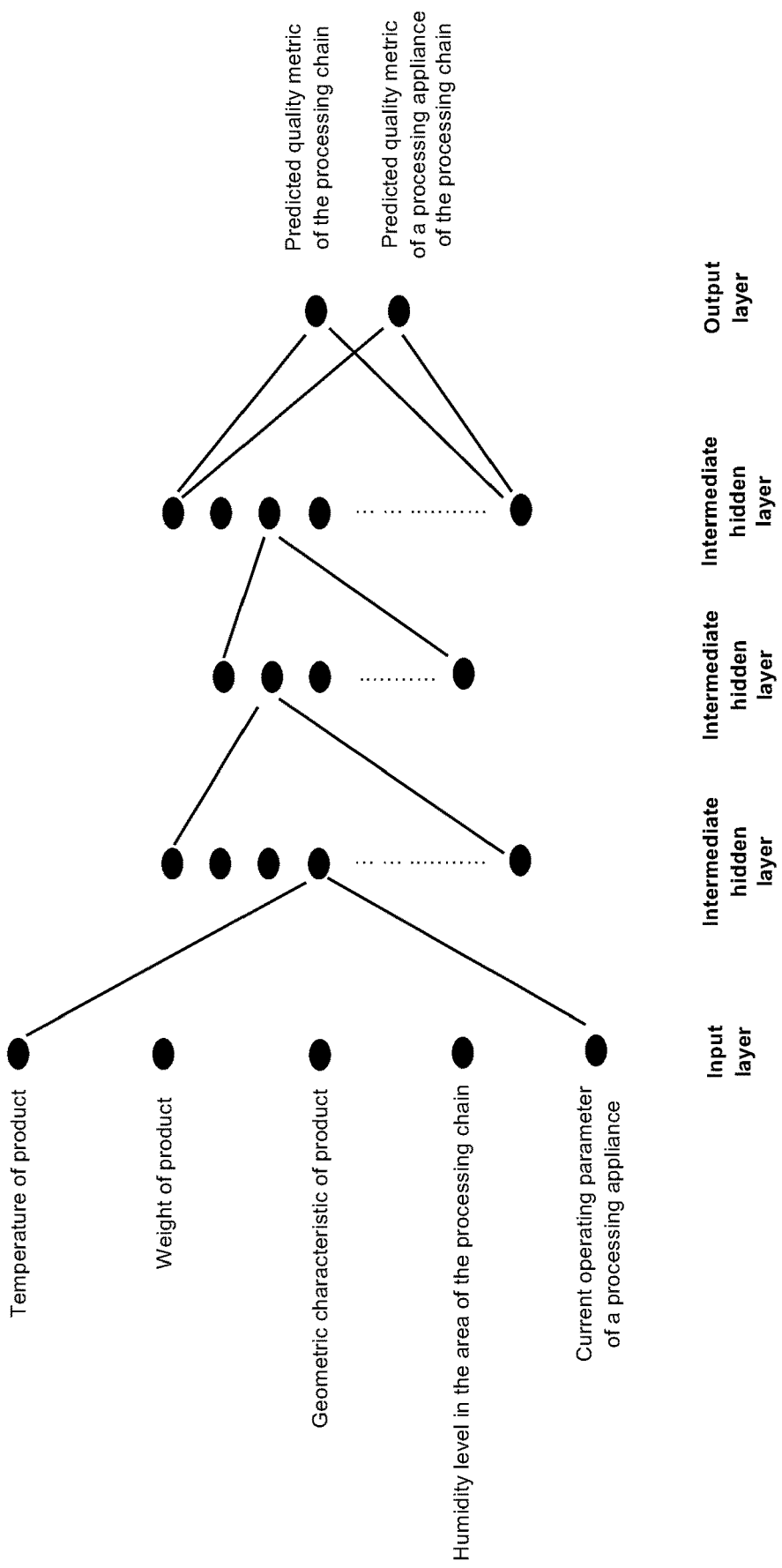
FIG. 13 is a detailed representation of a neural network implemented by the neural network inference engine of FIG. 12.

Reference is now made concurrently to FIGS. 11, 12 and 13, where FIG. 13 is a detailed representation of the neural network implemented by the neural network inference engine 112 schematically represented in FIG. 12. The neural network includes an input layer with five neurons for receiving inputs consisting of a temperature of the product, a weight of the product, a geometric characteristic of the product, a humidity level in the area of the processing chain 10 and a current operating parameter of a processing appliance (e.g. 400A) of the processing chain 10. The neural network includes an output layer with two neurons for outputting two outputs consisting of a predicted quality metric of the processing chain 10 and a predicted quality metric of a processing appliance (e.g. 400A) of the processing chain 10. The number of neurons of the input layer, the inputs, the number of neurons of the output layer and the outputs represented in FIG. 13 are for illustration purposes, and can be adapted to support all the use cases described in relation to the method 700. The neural network illustrated in FIG. 13 includes three intermediate hidden layers (for illustration purposes only) between the input layer and the output layer, and all the layers are fully connected. The number of neurons in each intermediate hidden layer may vary.

In a particular implementation, the outputs of the neural network at step 635 may also include one or more predicted yield (which has been previously described in relation to FIGS. 8, 9 and 10. In this case, the predictive model generated at step 705 is adapted to predict both quality metric(s) and yield(s) based on the inputs of the neural network.

Inference of Predicted $CO_2$ Footprint

Figure 14:
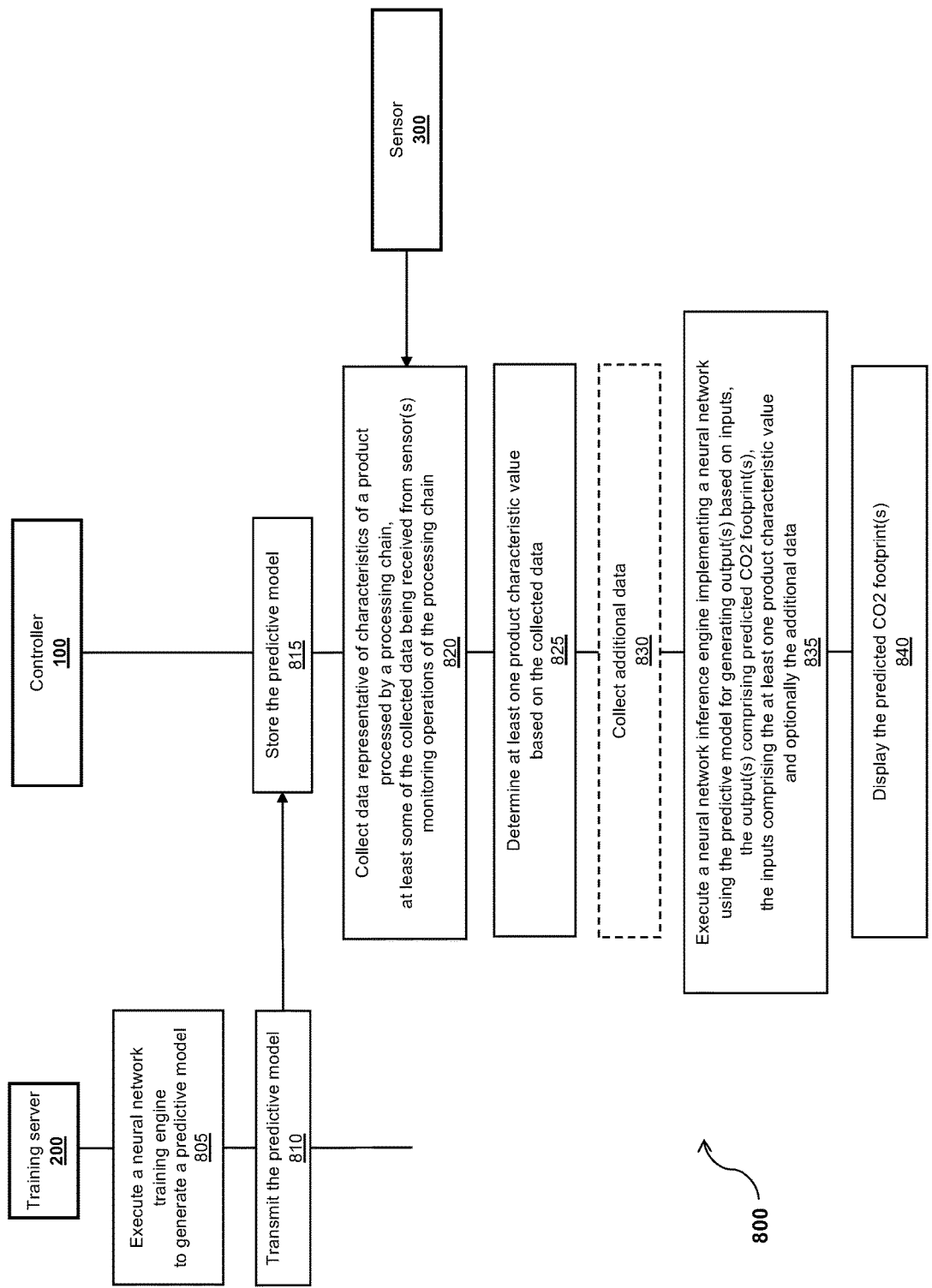
FIG. 14 illustrates a method using a neural network to infer a predicted $CO_2$ footprint for the processing chain of FIGS. 2 and 3.

Reference is now made concurrently to FIGS. 1, 2, 3, 4, 5 and 14. FIG. 14 represents a method 800 using a neural network for inferring predicted $CO_2$ footprint(s).

In the following, the neural network training engine 211 and the neural network inference engine 112 are used for respectively generating and using a predictive model capable of generating output(s) comprising the predicted $CO_2$ footprint(s) based on inputs. As mentioned previously, the predicted $CO_2$ footprint is defined for the processing chain 10 or for a given processing appliance (e.g. 400A) of the processing chain 10. The output(s) may comprise one or more predicted $CO_2$ footprint (e.g. one for the processing chain 10 and/or one for the processing appliance 400A). At least some of the inputs are similar to the inputs used in the context of method 500 represented in FIG. 5.

At least some of the steps of the method 800 are implemented by the controller 100, making use of the neural network to infer the predicted $CO_2$ footprint(s).

A dedicated computer program has instructions for implementing at least some of the steps of the method 800. The instructions are comprised in a non-transitory computer program product (e.g. the memory 120) of the controller 100. The instructions, when executed by the processing unit 110 of the controller 100, provide for making use of a neural network to infer predicted $CO_2$ footprint(s). The instructions are deliverable to the controller 100 via an electronically-readable media such as a storage media (e.g. CD-ROM, USB key, etc.), or via communication links (e.g. via a communication network through the communication interface 130).

The dedicated computer program product executed by the processing unit 110 comprises the neural network inference engine 112 and the control module 114.

The method 800 comprises the step 805 of executing the neural network training engine 211 (by the processing unit of the training server 200) to generate the predictive model. This step consists in training a neural network with a large sample of training data to generate the predictive model. The predictive model comprises the weights of the neural network, which are determined via this training process. Step 805 is similar to step 505 of the method 500. However, the predictive models generated at steps 805 and 505 are different.

The method 800 comprises the step 810 of transmitting the predictive model to the controller 100, via the communication interface of the training server 200.

The method 800 comprises the step 815 of storing the predictive model in the memory 120 of the controller 100. The predictive model is received via the communication interface 130 of the controller 100, and stored in the memory 120 by the processing unit 110.

The method 800 comprises the step 820 of collecting data representative of characteristics of the product processed by the processing chain 10. Step 820 is performed by the control module 114 executed by the processing unit 110. Step 820 is similar to step 520 of the method 500. At least some of the collected data are received via the communication interface 130 from the sensor(s) 300 monitoring operations of the processing chain 10. The data received from the sensor(s) 300 are (quasi) real time data, which may be different for each iteration of step 835. However, in some cases, these data may not evolve in (quasi) real time. Examples of such data have been provided previously in relation to the description of the sensors 300.

Optionally, some of the collected data representative of characteristics of the product are received via the communication interface 130 from one or more information server 450 as mentioned previously, and/or via the user interface 140. These data do not evolve in real time and can be stored in the memory 120 for a subsequent period of time once they are received. Thus, these data generally have the same value for a plurality of iterations of step 835. However, in some cases, these data may evolve in (quasi) real time. Examples of such data have been provided previously in relation to the description of the information server 450.

The method 800 comprises the step 825 of determining at least one product characteristic value based on the data collected at step 820. Step 825 is performed by the control module 114 executed by the processing unit 110. Step 825 is similar to step 525 of the method 500.

As mentioned previously in relation to step 525 of the method 500, the implementation of step 825 is adapted for each type of data collected at step 820. For a first given type of data collected at step 820, the determination of the product characteristic value simply consists in using the value collected at step 820 for the first given type of data. For a second given type of data collected at step 820, the determination of the product characteristic value consists in processing the value(s) collected at step 820 for the second given type of data to generate the corresponding product characteristic value. Furthermore, with respect to the data collected from the information server 450, these data can generally be used directly as product characteristic values without further processing.

The method 800 comprises the optional step 830 of collecting additional data. Step 830 is performed by the control module 114 executed by the processing unit 110. The additional data are not directly related to the product processed by the processing chain 10. Step 830 is similar to step 530 of the method 500.

As mentioned previously, an example of additional data includes at least one of a temperature/a humidity level/a lighting level, in the area where the processing chain 10 is operating. These additional data are received from dedicated sensors (different from the sensors 300) via the communication interface 130.

Another type of additional data includes at least one current operating parameter of the processing chain 10. For instance, the additional data include one or more current operating parameter of one or more processing appliance (e.g. 400A or 400B) of the processing chain 10. Examples of operating parameters have been provided previously.

Still another type of additional data includes one or more target yield. Target yields have been described previously. A target yield can be defined for the processing chain 10 or for a given processing appliance (e.g. 400A or 400B) of the processing chain 10.

Still another type of additional data includes one or more current yield. Current yields have been described previously. A current yield can be defined for the processing chain 10 or for a given processing appliance (e.g. 400A or 400B) of the processing chain 10.

Still another type of additional data includes one or more target quality metric. Target quality metrics have been described previously. A target quality metric can be defined for the processing chain 10 or for a given processing appliance (e.g. 400A or 400B) of the processing chain 10.

Still another type of additional data includes one or more current quality metric. Current quality metrics have been described previously. A current quality metric can be defined for the processing chain 10 or for a given processing appliance (e.g. 400A or 400B) of the processing chain 10.

Still another type of additional data includes one or more current $CO_2$ footprint. Current $CO_2$ footprints have been described previously. A current $CO_2$ footprint can be defined for the processing chain 10 or for a given processing appliance (e.g. 400A or 400B) of the processing chain 10.

The method 800 comprises the step 835 of executing the neural network inference engine 112 (by the processing unit 110). The neural network inference engine 112 implements a neural network using the predictive model (stored in memory 120 at step 815 and comprising the weights of the neural network) for generating one or more output based on inputs.

The one or more output comprises one or more predicted $CO_2$ footprint. Each predicted $CO_2$ footprint is a prediction of a value of a $CO_2$ footprint when the processing chain 10 is operating in conditions corresponding to the inputs of the neural network. As mentioned previously, a predicted $CO_2$ footprint can be defined for the processing chain 10 or for a given processing appliance (e.g. 400A or 400B) of the processing chain 10.

The inputs comprise the at least one product characteristic value determined at step 825. If the optional step 830 is performed, then the inputs further comprise the additional data collected at step 830.

As mentioned previously, instead of using a single value for a given type of input of the neural network, a series of consecutive values may be used as inputs. The neural network may also use convolution layer(s) and optionally pooling layer(s) following the convolution layer(s). For example, a one-dimension convolution is applied to a series of values corresponding to a given type of input and a two-dimension convolution is applied to several series of values corresponding to several types of input.

The method 800 comprises the step 840 of displaying the predicted $CO_2$ footprint(s) on the display 150 of the controller 100. Step 840 is performed by the control module 114 executed by the processing unit 110. Additionally, or complementarily, the one or more predicted $CO_2$ footprint is transmitted to one or more computing device via the communication interface 130. Still other types of processing may be applied to the predicted $CO_2$ footprint(s) generated at step 835.

Steps 825, optionally 830, 835 and 840 are repeated each time new data are collected at step 820. As mentioned previously, configurable thresholds may be used for the data received at step 820, so that a change in the value of a given type of data is not taken into consideration (steps 825, optionally 830, 835 and 840 are not performed) as long as the change remains within the boundaries of the corresponding threshold(s).

The training phase, which results in the generation of the predictive model, is similar to the training phase described in the context of the method 500. During the training phase, the neural network training engine 211 is trained with a plurality of inputs and a corresponding plurality of outputs. Each input comprises product characteristic value(s) and optionally additional data as mentioned previously, and each corresponding output comprises predicted $CO_2$ footprint(s).

As is well known in the art of neural network, during the training phase, the neural network implemented by the neural network training engine 211 adjusts its weights. Furthermore, during the training phase, the number of layers of the neural network and the number of nodes per layer can be adjusted to improve the accuracy of the model. At the end of the training phase, the predictive model generated by the neural network training engine 211 includes the number of layers, the number of nodes per layer, and the weights.

As mentioned previously, the inputs and outputs for the training phase of the neural network can be collected through an experimental process. For example, a plurality of combinations of product characteristic values are tested. For each combination, one or more corresponding $CO_2$ footprint is determined. In addition to the product characteristic values, each combination may include additional parameters representative of the current state of the processing chain 10 and/or of a given processing appliance (e.g. 400A) of the processing chain 10. Such additional parameters have been mentioned previously and include current operating parameters of a given processing appliance, a current yield, a current quality metric, a current $CO_2$ footprint, etc. The neural network training engine 211 is trained with the combination of inputs (product characteristic values and optional additional parameters) and corresponding output(s) (one or more corresponding determined $CO_2$ footprint). The $CO_2$ footprints (s) corresponding to the aforementioned combinations of inputs may also be determined for various values of a target yield or a target quality metric, which are also respectively used as input for the training of the neural network. For example, the $CO_2$ footprints are determined for a target yield varying from 70 to 90 percent by increments of approximatively 1 percent. In this case, the target yield is also used as an input for the training of the neural network.

Figure 15:
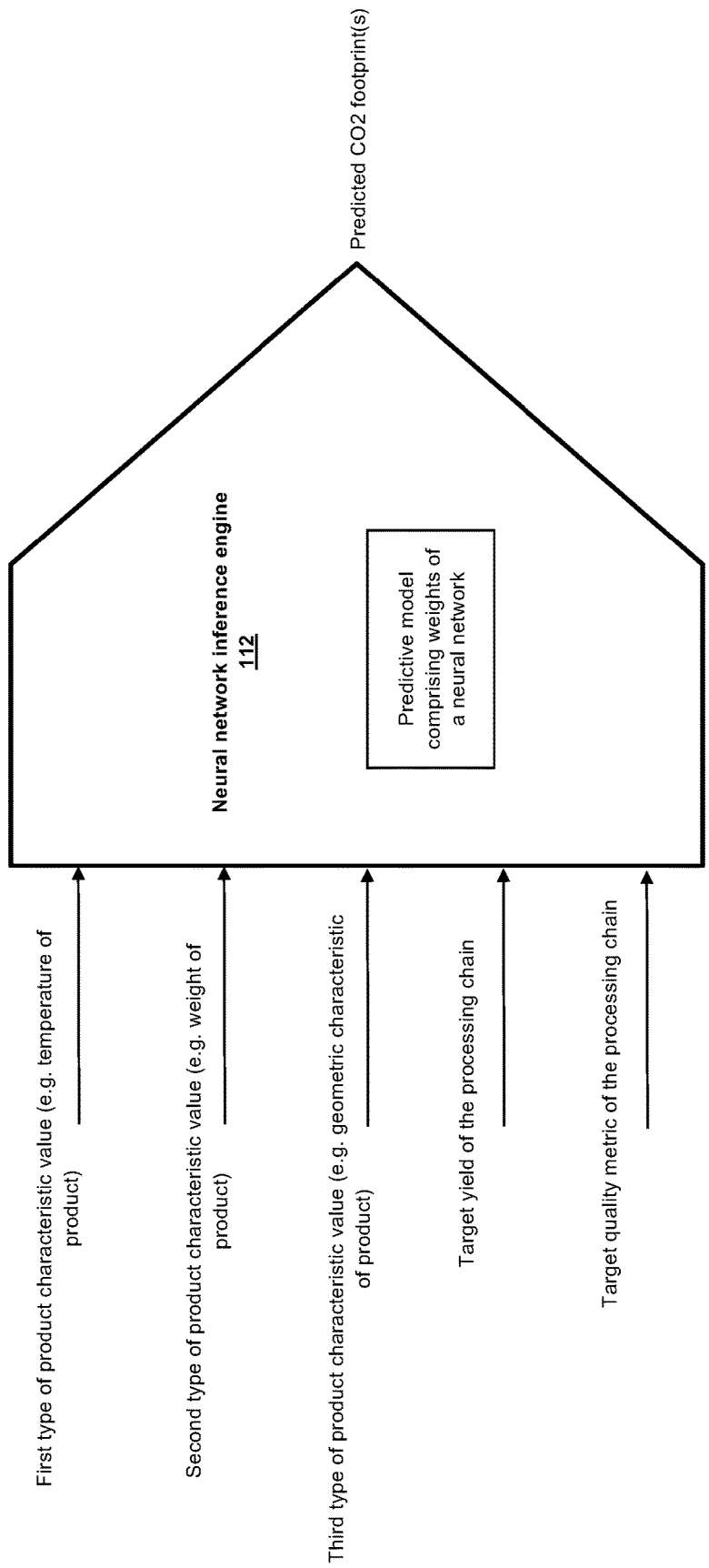
FIG. 15 is a schematic representation of a neural network inference engine executed by the controller of FIGS. 2, 3 and 4 when implementing the method of FIG. 14.

Reference is now made to FIGS. 4, 14 and 15, where FIG. 15 illustrates the neural network inference engine 112 with its inputs and its output(s). FIG. 15 corresponds to the neural network inference engine 112 represented in FIG. 4 and executed at step 835 of the method 800 represented in FIG. 14. The inputs represented in FIG. 15 are for illustration purposes only, and correspond to one exemplary combination of the previously described types of inputs.

Figure 16:
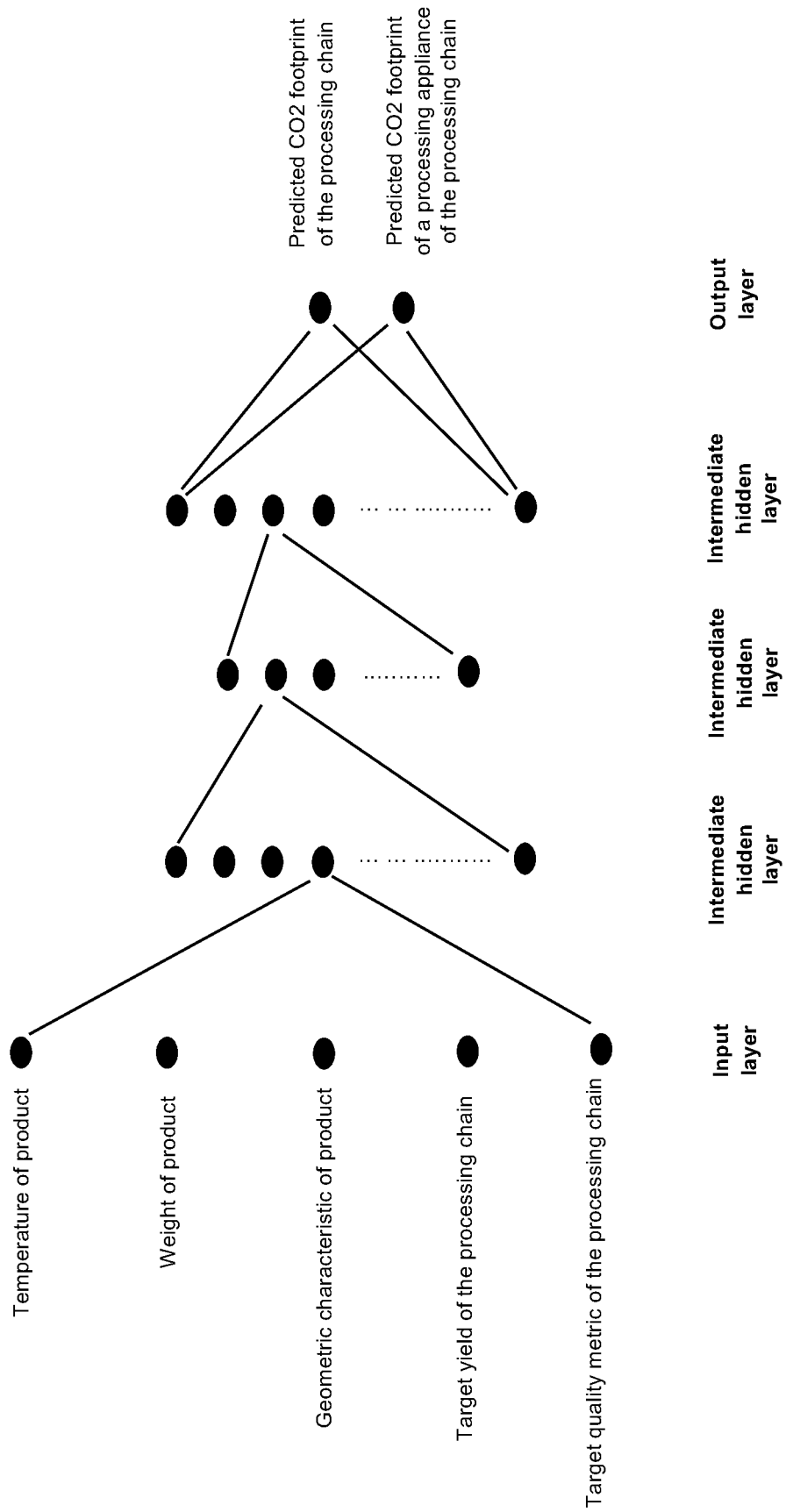
FIG. 16 is a detailed representation of a neural network implemented by the neural network inference engine of FIG. 15.

Reference is now made concurrently to FIGS. 14, 15 and 16, where FIG. 16 is a detailed representation of the neural network implemented by the neural network inference engine 112 schematically represented in FIG. 15. The neural network includes an input layer with five neurons for receiving inputs consisting of a temperature of the product, a weight of the product, a geometric characteristic of the product, a target yield of the processing chain 10 and a target quality metric of the processing chain 10. The neural network includes an output layer with two neurons for outputting two outputs consisting of a predicted $CO_2$ footprint of the processing chain 10 and a predicted $CO_2$ footprint of a processing appliance (e.g. 400A) of the processing chain 10. The number of neurons of the input layer, the inputs, the number of neurons of the output layer and the outputs represented in FIG. 16 are for illustration purposes, and can be adapted to support all the use cases described in relation to the method 800. The neural network illustrated in FIG. 16 includes three intermediate hidden layers (for illustration purposes only) between the input layer and the output layer, and all the layers are fully connected. The number of neurons in each intermediate hidden layer may vary.

In a particular implementation, the outputs of the neural network at step 835 may also include one or more predicted yield (which has been previously described in relation to FIGS. 8, 9 and 10. In this case, the predictive model generated at step 805 is adapted to predict both $CO_2$ footprint(s) and yield(s) based on the inputs of the neural network. Alternatively or complementarily, the outputs of the neural network at step 835 may also include one or more predicted quality metric (which has been previously described in relation to FIGS. 11, 12 and 13. In this case, the predictive model generated at step 805 is adapted to predict both $CO_2$ footprint(s) and quality metric(s) based on the inputs of the neural network.

Usage of Machine Learning to Determine Product Characteristic Value(s)

Reference is now made concurrently to FIGS. 4, 5, 8, 11 and 14; and more specifically to steps 525, 625, 725 and 825 of respective methods 500, 600, 700 and 800.

The determination of one or more of the product characteristic value(s) (respectively at step 525, 625, 725 or 825) based on the collected data (respectively at step 520, 620, 720 or 820) makes use of machine learning technology.

In this implementation, a first stage of machine learning technology is applied to the collected data to generate one or more of the product characteristic value(s). As described previously, a second stage of machine learning technology is used at steps 535, 635, 735 and 835.

Following are examples of sensors 300 collecting data, which are processed by a machine learning engine to perform product characteristic values (respectively at step 525, 625, 725 or 825).

A hyperspectral imaging and infrared spectroscopy sensor collects data, which are processed by a Partial Least Squares Discriminant Analysis (PLSDA) engine, to perform variety identification of a product (e.g. varieties of sweet potatoes).

A laser-light backscattering imaging sensor collects data, which are processed by a Linear Discriminant Analysis (LDA) engine, to perform discrimination of a product (e.g. potatoes) from clods and stones.

A depth imaging (machine vision) sensor collects data, which are processed by a VMA engine, to perform at least one of length, width, thickness, mass and volume measurements of a product (e.g. potatoes).

A Raman spectroscopy sensor collects data, which are processed by a Partial Least Squares Regression (PLSR)/Principal Component Analysis (PCA) engine, to perform moisture and carotenoid content measurements of a product (e.g. sweet potatoes).

A near-infrared (NIR) spectroscopy sensor collects data, which are processed by an LDA/PLSR engine, to perform disease detection of a product (e.g. zebra chip disease detection for potatoes).

A laser-light backscattering imaging sensor collects data, which are processed by an PLSR/PCA engine, to perform moisture content measurements of a product (e.g. sweet potatoes).

An infrared spectroscopy sensor collects data, which are processed by an MPLS/PCA engine, to perform measurements of at least one of dry matter, total soluble solid content, apex and flesh texture, color coordinates of a product (e.g. sweet potatoes).

A hyperspectral imaging sensor collects data, which are processed by an Super-Vector Machine (SVM) engine. to perform bruises detection of a product (e.g. potatoes).

A hyperspectral imaging sensor collects data, which are processed by an PLSR engine, to perform chromaticity and moisture content measurements of a product (e.g. potatoes).

A laser-light backscattering imaging sensor collects data, which are processed by an Artificial Neural Network (ANN) engine, to perform moisture content and firmness measurements of a product (e.g. potatoes).

A hyperspectral imaging sensor collects data, which are processed by an PCA/PLSDA engine, to perform moisture content measurements of a product (e.g. potatoes or sweet potatoes).

A visible-near-infrared (vis-NIR) and short-wave infrared (SWIR) hyperspectral imaging sensor collects data, which are processed by an PLSDA engine, to perform black spots detection of a product (e.g. potatoes).

A dielectric spectroscopy sensor collects data, which are processed by an PLSR engine, to perform dry matter content measurements of a product (e.g. potatoes).

A NIR spectroscopy sensor collects data, which are processed by an ANN/LDA/PLSR engine, to perform sugar content measurements of a product (e.g. potatoes).

A dielectric spectroscopy and infrared thermography sensor collect data, which are processed by an TA engine, to perform freezing process detection of a product (e.g. potatoes).

An impedance spectroscopy sensor collects data, which are processed by an Dragonfly Algorithm (DA)/PCA engine, to perform texture and microstructure measurements of a product (e.g. potatoes).

A magnetic resonance imaging sensor collects data, which are processed by an PLSR/PCA engine, to perform sensory texture properties measurements of a product (e.g. potatoes).

All of the aforementioned machine learning technologies are well known in the art. A person skilled in the art would readily understand how to apply any of these technologies to the collected data, in order to generate the corresponding product characteristic values.

Although the present disclosure has been described hereinabove by way of non-restrictive, illustrative embodiments thereof, these embodiments may be modified at will within the scope of the appended claims without departing from the spirit and nature of the present disclosure.

What is claimed is:

1. A computing device comprising:
   at least one communication interface;
   memory for storing a predictive model; and
   a processing unit comprising one or more processor configured to:
      collect data representative of characteristics of a product processed by a processing chain, at least some of the collected data being received via the at least one communication interface from one or more sensor monitoring operations of the processing chain;
      determine at least one product characteristic value based on the collected data;
      collect additional data, the additional data comprising at least one current yield, each current yield being defined for one of the processing chain or a processing appliance of the processing chain;
      execute a machine learning inference engine, the machine learning inference engine using the predictive model for inferring one or more output based on inputs, the inputs comprising the at least one product characteristic value and the at least one current yield, the one or more output comprising one or more command for controlling at least one processing appliance of the processing chain; and
      transmit via the at least one communication interface the one or more command to the at least one processing appliance of the processing chain.

2. The computing device of claim 1, wherein the machine learning inference engine is a neural network inference engine implementing a neural network using the predictive model for inferring the one or more output based on the inputs, the predictive model comprising weights of the neural network.

3. The computing device of claim 2, wherein the neural network comprises an input layer, followed by fully connected hidden layers, followed by an output layer; the input layer comprising at least one neuron receiving the at least one product characteristic value; the output layer comprising one or more neuron outputting the one or more command; the weights of the neural network being applied to the fully connected hidden layers.

4. The computing device of claim 1, wherein the processing chain is located in a food factory and the product is a food product.

5. The computing device of claim 1, wherein the one or more command controls a functionality implemented by the at least one processing appliance, the functionality comprising inspecting, sorting, cleaning, cutting, peeling, slicing, blending, mixing, blanching, cooking, baking, frying, heating, cooling, freezing, humidifying or packaging.

6. The computing device of claim 1, wherein at least some of the collected data representative of characteristics of the product processed by the processing chain are received via the at least one communication interface from one or more information server.

7. The computing device of claim 1, wherein the at least one product characteristic value comprises at least one of the following: a temperature of the product, a humidity level of the product, a geometric characteristic of the product, a weight of the product, a tensile strength of the product, an internal pressure of the product, a stock keeping unit (SKU) of the product, and a defect measurement for the product.

8. The computing device of claim 1, wherein the processing unit further collects additional data, the additional data comprising at least one environmental characteristic value; the at least one environmental characteristic value comprising at least one of a temperature of an area where the processing chain is located, a humidity level of the area where the processing chain is located and a lighting level of the area where the processing chain is located; the inputs of the machine learning inference engine further comprising the at least one environmental characteristic value.

9. The computing device of claim 1, wherein the processing unit further collects additional data, the additional data comprising at least one current operating parameter of at least one processing appliance of the processing chain; the inputs of the machine learning inference engine further comprising the at least one current operating parameter.

10. The computing device of claim 1, wherein the additional data further comprise at least one target yield; each target yield being defined for one of the processing chain or a processing appliance of the processing chain; the inputs of the machine learning inference engine further comprising the at least one target yield.

11. The computing device of claim 1, wherein the additional data further comprise at least one target quality metric; each target quality metric being defined for one of the processing chain or a processing appliance of the processing chain; the inputs of the machine learning inference engine further comprising the at least one target quality metric.

12. The computing device of claim 1, wherein the additional data further comprise at least one current quality metric; each current quality metric being defined for one of the processing chain or a processing appliance of the processing chain; the inputs of the machine learning inference engine further comprising the at least one current quality metric.

13. The computing device of claim 1, wherein the processing unit further collects additional data, the additional data comprising at least one target carbon dioxide ($CO_2$) footprint; each target $CO_2$ footprint being defined for one of the processing chain or a processing appliance of the processing chain; the inputs of the machine learning inference engine further comprising the at least one target $CO_2$ footprint.

14. The computing device of claim 1, wherein the processing unit further collects additional data, the additional data comprising at least one current $CO_2$ footprint; each current $CO_2$ footprint being defined for one of the processing chain or a processing appliance of the processing chain; the inputs of the machine learning inference engine further comprising the at least one current $CO_2$ footprint.

15. The computing device of claim 1, wherein the determination of one or more among the at least one product characteristic value based on the collected data uses another machine learning inference engine.

16. A method using machine learning to optimize operations of a processing chain, the method comprising:
    storing a predictive model in a memory of a computing device;
    collecting by a processing unit of the computing device data representative of characteristics of a product processed by the processing chain, at least some of the collected data being received via at least one communication interface of the computing device from one or more sensor monitoring operations of the processing chain;
    determining by the processing unit of the computing device at least one product characteristic value based on the collected data;
    collecting by the processing unit of the computing device additional data, the additional data comprising at least one current yield, each current yield being defined for one of the processing chain or a processing appliance of the processing chain;
    executing by the processing unit of the computing device a machine learning inference engine, the machine learning inference engine using the predictive model for inferring one or more output based on inputs, the inputs comprising the at least one product characteristic value and the at least one current yield, the one or more output comprising one or more command for controlling at least one processing appliance of the processing chain; and
    transmitting by the processing unit of the computing device via the at least one communication interface of the computing device the one or more command to the at least one processing appliance of the processing chain.

17. The method of claim 16, wherein the machine learning inference engine is a neural network inference engine implementing a neural network using the predictive model for inferring the one or more output based on the inputs, the predictive model comprising weights of the neural network.

18. The method of claim 16, wherein the processing chain is located in a food factory and the product is a food product.

19. The method of claim 16, wherein the at least one product characteristic value comprises at least one of the following: a temperature of the product, a humidity level of the product, a geometric characteristic of the product, a weight of the product, a tensile strength of the product, an internal pressure of the product, a stock keeping unit (SKU) of the product, and a defect measurement for the product.

20. The method of claim 16, wherein the determination of one or more among the at least one product characteristic value based on the collected data uses another machine learning inference engine.

21. A non-transitory computer-readable medium comprising instructions executable by a processing unit of a computing device, the execution of the instructions by the processing unit providing for using machine learning to optimize operations of a processing chain by:
    storing a predictive model in a memory of the computing device;
    collecting data representative of characteristics of a product processed by the processing chain, at least some of the collected data being received via at least one communication interface of the computing device from one or more sensor monitoring operations of the processing chain;

determining at least one product characteristic value based on the collected data;

collecting additional data, the additional data comprising at least one current yield, each current yield being defined for one of the processing chain or a processing appliance of the processing chain;

executing a machine learning inference engine, the machine learning inference engine using the predictive model for inferring one or more output based on inputs, the inputs comprising the at least one product characteristic value and the at least one current yield, the one or more output comprising one or more command for controlling at least one processing appliance of the processing chain; and transmitting via the at least one communication interface of the computing device the one or more command to the at least one processing appliance of the processing chain.

* * * * *